US012115269B2

(12) United States Patent
McCanless et al.

(10) Patent No.: US 12,115,269 B2
(45) Date of Patent: *Oct. 15, 2024

(54) TECHNIQUES FOR DIRECTING ULTRAVIOLET ENERGY TOWARDS A MOVING SURFACE

(71) Applicant: ABL IP Holding LLC, Atlanta, GA (US)

(72) Inventors: Forrest Starnes McCanless, Oxford, GA (US); Charles Richard Shoop, Jr., Blythewood, SC (US); Yan Rodriguez, Suwanee, GA (US)

(73) Assignee: ABL Holding Holding LLC, Atlanta, GA (US)

( * ) Notice: Subject to any disclaimer, the term of this patent is extended or adjusted under 35 U.S.C. 154(b) by 748 days.

This patent is subject to a terminal disclaimer.

(21) Appl. No.: 17/313,204

(22) Filed: May 6, 2021

(65) Prior Publication Data

US 2022/0096676 A1    Mar. 31, 2022

Related U.S. Application Data

(60) Provisional application No. 63/085,000, filed on Sep. 29, 2020.

(51) Int. Cl.
*A61L 2/10* (2006.01)
*B65G 45/00* (2006.01)

(52) U.S. Cl.
CPC ............... *A61L 2/10* (2013.01); *B65G 45/00* (2013.01); *A61L 2202/11* (2013.01); *A61L 2202/14* (2013.01); *A61L 2202/17* (2013.01)

(58) Field of Classification Search
CPC .......... A61L 2/10; A61L 2/24; A61L 2202/11; A61L 2202/14; A61L 2202/17;

(Continued)

(56) References Cited

U.S. PATENT DOCUMENTS 3,571,939 A    3/1971    Paul
3,915,180 A    10/1975   Jacobs
(Continued)

FOREIGN PATENT DOCUMENTS

CN    2705737    6/2005
JP    1094583    4/1998
(Continued)

OTHER PUBLICATIONS

J. Johnson, "What Is a Relay and Why Are They So Important", Amperite webpage published Apr. 16, 2019 (Year: 2019).*

(Continued)

*Primary Examiner* — Jennifer Wecker
*Assistant Examiner* — Brady C Pilsbury
(74) *Attorney, Agent, or Firm* — Kilpatrick Townsend & Stockton LLP

(57) ABSTRACT

An ultraviolet ("UV") emission device may emit energy towards a movable surface of a conveyor system. A housing of the UV emission device may attach to a frame of the conveyor system. A lateral edge of the housing may extend across the moveable surface. The housing and a portion of the moveable surface may be inclined with respect to the frame. A barrier bracket of the UV emission device may support an absorptive barrier along the lateral edge, the absorptive barrier configured to contact the moveable surface. In a first position of the barrier bracket, the absorptive barrier contacts the moveable surface and the barrier bracket activates an interlock switch. In a second position of the barrier bracket, the barrier bracket deactivates the interlock switch. Responsive to deactivation of the interlock switch, a controller may provide a control signal to decrease power to the UV energy emission element.

25 Claims, 26 Drawing Sheets

(58) Field of Classification Search
CPC .............. A61L 2202/122; B65G 45/00; B65G 2207/26; B65G 2207/40; B65G 2207/48; B65G 43/00; B65G 43/02; B65G 43/10

See application file for complete search history.

(56) References Cited

U.S. PATENT DOCUMENTS

| | | | |
|---|---|---|---|
| 4,229,658 A | 10/1980 | Gonser | |
| 4,421,987 A | 12/1983 | Herold | |
| 4,448,750 A | 5/1984 | Fuesting | |
| 4,867,796 A | 9/1989 | Asmus et al. | |
| 4,871,559 A | 10/1989 | Dunn et al. | |
| 5,034,235 A | 7/1991 | Dunn et al. | |
| 5,607,711 A | 3/1997 | Lagunas-Solar | |
| 5,959,365 A * | 9/1999 | Mantini | B60C 23/0408 180/290 |
| 6,030,653 A | 2/2000 | Rosenthal | |
| 6,039,928 A | 3/2000 | Roberts | |
| 6,054,097 A | 4/2000 | Mass et al. | |
| 6,057,917 A | 5/2000 | Petersen et al. | |
| 6,087,141 A | 7/2000 | Margolis-Nunno et al. | |
| 6,254,625 B1 | 7/2001 | Rosenthal et al. | |
| 6,343,400 B1 | 2/2002 | Massholder et al. | |
| 6,623,272 B2 | 9/2003 | Clemans | |
| 6,790,409 B1 | 9/2004 | Nakamura et al. | |
| 6,902,397 B2 | 6/2005 | Farrell et al. | |
| 6,902,563 B2 | 6/2005 | Wilkens et al. | |
| 8,398,264 B2 | 3/2013 | Anderson et al. | |
| 8,481,985 B2 | 7/2013 | Neister | |
| 8,624,203 B2 * | 1/2014 | Tullo | A61L 2/10 250/492.1 |
| 8,753,575 B2 | 6/2014 | Neister | |
| 8,838,228 B2 | 9/2014 | Beisang, III et al. | |
| 8,975,605 B2 | 3/2015 | Neister | |
| 9,039,966 B2 | 5/2015 | Anderson et al. | |
| 9,333,274 B2 | 5/2016 | Peterson et al. | |
| 9,700,542 B2 | 7/2017 | Breslin et al. | |
| 9,700,641 B2 | 7/2017 | Hawkins et al. | |
| 9,700,642 B2 | 7/2017 | Neister | |
| 9,839,706 B2 | 12/2017 | Anderson et al. | |
| 10,281,326 B2 | 5/2019 | Ramer et al. | |
| 10,458,844 B2 | 10/2019 | Ramer et al. | |
| 10,933,150 B1 * | 3/2021 | Robinson | A61L 2/10 |
| 2002/0015662 A1 | 2/2002 | Hlavinka | |
| 2002/0173833 A1 | 11/2002 | Korman et al. | |
| 2003/0012687 A1 | 1/2003 | Macphee et al. | |
| 2003/0018373 A1 * | 1/2003 | Eckhardt | A61N 5/0624 607/94 |
| 2003/0103866 A1 | 6/2003 | Wang et al. | |
| 2003/0153962 A1 | 8/2003 | Cumbie | |
| 2003/0161756 A1 | 8/2003 | Heldebrant et al. | |
| 2004/0005251 A1 | 1/2004 | Branham | |
| 2004/0039242 A1 | 2/2004 | Tolkoff et al. | |
| 2004/0131497 A1 | 7/2004 | Lengsfeld et al. | |
| 2005/0064371 A1 | 3/2005 | Soukos et al. | |
| 2011/0308917 A1 * | 12/2011 | Lathem | A61L 2/10 250/492.1 |
| 2012/0056102 A1 * | 3/2012 | Stanley | A61L 2/10 250/455.11 |
| 2013/0264175 A1 * | 10/2013 | Landrum | B65G 43/02 198/805 |
| 2014/0341777 A1 * | 11/2014 | Deshays | G01K 13/00 250/354.1 |
| 2015/0335246 A1 | 11/2015 | Rains, Jr. et al. | |
| 2019/0247528 A1 | 8/2019 | Rodriguez | |
| 2019/0262487 A1 * | 8/2019 | Gil | A61L 2/202 |
| 2020/0073199 A1 | 3/2020 | Lin et al. | |
| 2020/0197550 A1 * | 6/2020 | Barron | A61L 2/24 |
| 2020/0289687 A1 | 9/2020 | Riley et al. | |
| 2021/0330832 A1 * | 10/2021 | Dobbins | G07F 9/10 |
| 2022/0096675 A1 | 3/2022 | Mccanless et al. | |
| 2022/0096676 A1 | 3/2022 | Mccanless et al. | |
| 2022/0096681 A1 | 3/2022 | Mccanless et al. | |

FOREIGN PATENT DOCUMENTS

| | | |
|---|---|---|
| JP | 10156349 | 6/1998 |
| JP | 2001261518 | 9/2001 |
| JP | 2003260134 | 9/2003 |
| JP | 2004275335 | 10/2004 |
| JP | 2005137822 | 6/2005 |
| WO | 2004080494 | 9/2004 |

OTHER PUBLICATIONS

U.S. Appl. No. 17/485,677, "Notice of Allowance", Aug. 22, 2023, 8 pages.

U.S. Appl. No. 17/313,193, "Notice of Allowance", Oct. 26, 2023, 8 pages.

CA 3,132,416, "Office Action," Feb. 14, 2023, 6 pages.

Acuity Brands Announces Agreement with Ushio America, Inc., Available online at: http://www.globenewswire.com/news-release/2020/06/01/2041460/0/en/Acuity-Brands-Announces-Agreement-with-Ushio-America-Inc.html, Jun. 1, 2020, 2 pages.

Cleanse® Downlight Owner's Manual, Healthe by Lighting Science, 2020, 3 pages.

Technology for Improving Health, High Energy Ozone, LLC—UV Sterilization Technology, Aug. 8, 2018, 14 pages.

U.S. Appl. No. 17/005,971, filed Aug. 28, 2020.

U.S. Appl. No. 17/186,832, filed Feb. 26, 2021.

U.S. Appl. No. 17/337,849, filed Jun. 3, 2021.

Buonanno et al., Germicidal Efficacy and Mammalian Skin Safety of 222-nm UV Light, Radiation Research, vol. 187, No. 4, Apr. 2017, pp. 483-491.

Bintsis et al., Existing and Potential Applications of Ultraviolet Light in the Food Industry—a Critical Review, Journal of the Science of Food and Agriculture, vol. 80, No. 6, May 1, 2000, pp. 637-645.

Eisenstark, Mutagenic and Lethal Effects of Near-ultraviolet Radiation (290-400 NM) on Bacteria and Phage, Environmental and molecular mutagenesis, vol. 10, No. 3, Jan. 1, 1987, pp. 317-337.

Feuerstein et al., Phototoxic Effect of Visible Light on Porphyromonas Gingivalis and Fusobacterium Nucleatum: an in Vitro Study, Photochemistry and Photobiology, vol. 80, No. 3, Nov.-Dec. 2004, pp. 412-415.

Hollaender, Effect of Long Ultraviolet and Short Visible Radiation (3500 to 4900x) on *Escherichia coli*, Journal of bacteriology, vol. 46, No. 6, Dec. 1943, pp. 531-541.

Webb et al., Mutagenic Effects of Near Ultraviolet and Visible Radiant Energy on Continuous Cultures of *Escherichia coli*, Photochemistry and photobiology, vol. 12, No. 6, Dec. 1970, pp. 457-468.

U.S. Appl. No. 17/313,193, "Non-Final Office Action," Jul. 20, 2023, 7 pages.

U.S. Appl. No. 17/485,677, "Non-Final Office Action," Aug. 4, 2023, 6 pages.

* cited by examiner

TECHNIQUES FOR DIRECTING ULTRAVIOLET ENERGY TOWARDS A MOVING SURFACE

RELATED APPLICATIONS

The present application claims priority to U.S. provisional application No. 63/085,000 entitled "Techniques for Directing Ultraviolet Energy Towards a Moving Surface," filed Sep. 29, 2020, which is incorporated by reference herein in its entirety. The present application is related to U.S. application Ser. No. 17/313,193 filed on May 6, 2021.

TECHNICAL FIELD

This disclosure relates generally to the field of fixtures for emitting ultraviolet energy, and more specifically relates to an emission device configured to direct ultraviolet energy towards a moving surface.

BACKGROUND

Conveyor systems may be used in a wide variety of environments, such as retail checkout locations, manufacturing facilities, or warehouses. A conveyor system may be exposed to a wide variety of materials and users that can introduce pathogens to surfaces of the conveyor system. For example, a conveyor belt that is installed in a grocery store environment may be exposed to fluids or food debris from groceries that are placed on the belt. In some cases, the fluids or food debris may carry or encourage accumulation of pathogens on the surface of the conveyor belt. In addition, the example conveyor belt may be exposed to pathogens from users of the grocery store, such as exposure to coughing, money or other objects placed on the belt, airborne droplets, or other sources of pathogens that may be carried or encouraged by people using a conveyor system. Contemporary techniques to disinfect surfaces of a conveyor system may be inefficient or otherwise unsuitable for a conveyor system environment. For example, manual cleaning of the example grocery store conveyor belt may require a relatively high degree of time and effort from employees in the grocery store. In addition, manual cleaning efforts may be inconsistent among a group of people, and may result in inconsistent disinfection of the conveyor system surface. Automated contemporary techniques, such as spray cleaning systems, may be unsuitable for some conveyor system environments. For example, an automated spray cleaning system implemented in a warehouse environment could potentially damage items that are carried via a conveyor system, such as water damage to cardboard boxes or paper items.

In some cases, ultraviolet ("UV") energy may have a disinfecting effect on surfaces. It may be beneficial to develop techniques to expose surfaces of a conveyor system to UV energy.

SUMMARY

According to certain embodiments, a UV emission device for a conveyor system may include a housing, an energy emission element arranged within the housing, a barrier bracket, and an absorptive barrier. The housing may be configured to attach to a frame of the conveyor system, within an interior cavity of the frame. The frame may support a moveable surface of the conveyor system, such that a return surface of the moveable surface is located within the interior cavity. The housing may have a lateral edge configured to extend across the return surface within the interior cavity and a longitudinal edge configured to extend along the return surface within the interior cavity. A first end of the longitudinal edge may be arranged at a first location on the frame and a second end of the longitudinal edge may be arranged at a second location on the frame. The lateral edge may intersect the longitudinal edge at the first end. The return surface may contact the longitudinal edge at the first end and at the second end. The longitudinal edge may have a first angle between the first end and at the second end. A portion of the return surface between the first end and at the second end may have the first angle. Each of the longitudinal edge and the return surface may have a respective incline. The respective inclines may be in a particular direction with respect to the frame. The barrier bracket may be arranged along the lateral edge. The barrier bracket may have a first position and a second position. The absorptive barrier may be supported via the barrier bracket. The absorptive barrier may be configured to contact the return surface along the lateral edge of the housing. In the first position of the barrier bracket, the absorptive barrier contacts the return surface and the barrier bracket activates an interlock switch. In the second position of the barrier bracket, the barrier bracket deactivates the interlock switch.

According to certain embodiments, a control system for a UV emission element may include a controller, a power regulator, and an interlock switch. The power regulator may be configured to provide power to the UV emission element. The interlock switch may be configured to indicate a contact status between a housing of the UV emission element and a moveable surface of a conveyor system. The controller may be configured for identifying a status of the interlock switch, responsive to receiving a status data signal from the interlock switch. A first value of the status data signal may indicate a closed status of the interlock switch. A second value of the status data signal may indicate an open status of the interlock switch. The controller may be further configured for, based on the identified status of the interlock switch, providing a control signal to modify power output by the power regulator. Responsive to identifying the closed status of the interlock switch, the controller may provide a first control signal configuring the power regulator to provide power to the UV energy emission element. Responsive to identifying the open status of the interlock switch, the controller may provide a second control signal configuring the power regulator to decrease power to the UV energy emission element.

These illustrative embodiments are mentioned not to limit or define the disclosure, but to provide examples to aid understanding thereof. Additional embodiments are discussed in the Detailed Description, and further description is provided there.

BRIEF DESCRIPTION OF THE DRAWINGS

Features, implementations, and advantages of the present disclosure are better understood when the following Detailed Description is read with reference to the accompanying drawings, where.

DETAILED DESCRIPTION

Figure 1:
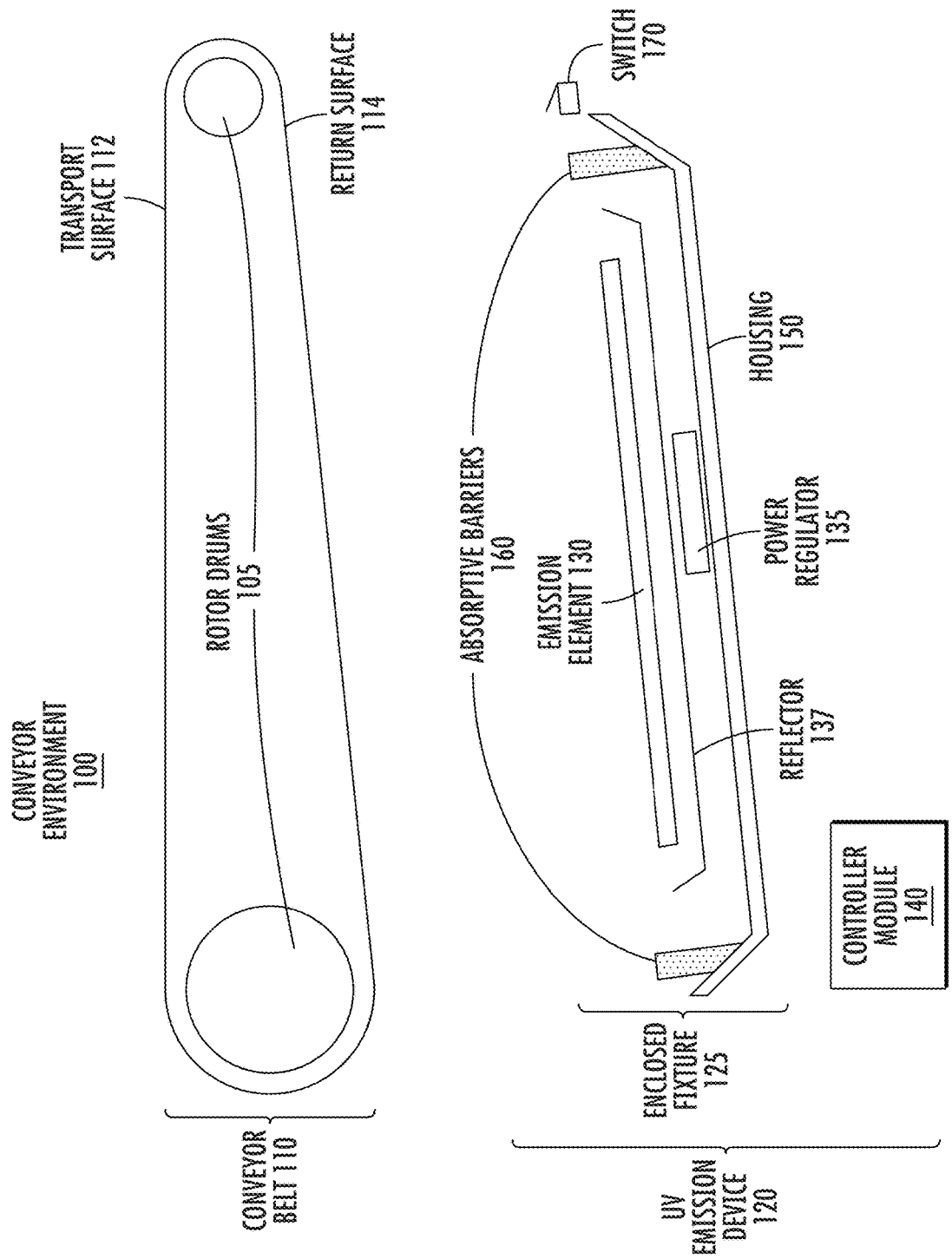
FIG. 1 is a block diagram depicting an example of a conveyor environment including one or more conveyor systems and one or more UV emission devices, according to certain implementations.

As discussed above, prior techniques for disinfecting surfaces of conveyor systems do not provide efficient disinfection for conveyor systems in a wide variety of conveyor environments. Certain implementations described herein provide for techniques to direct UV energy towards conveyor systems, including conveyor systems in a wide variety of conveyor environments. These techniques may provide consistent exposure of surfaces of a conveyor system to UV energy, including UV energy that may have a disinfecting effect. In addition, these techniques may reduce time and expenses related to manual cleaning of conveyor systems, such as manual cleaning by employees or other users within the conveyor environment.

In some implementations, aspects of these techniques may provide a circuit interrupt that prevents generation of UV energy. In some aspects, a circuit interrupt may improve safety of the described techniques, such as by preventing emission of UV energy outside of an enclosure of a UV emission device.

The following examples are provided to introduce certain implementations of the present disclosure. A UV emission device may be arranged with a conveyor system, such as a conveyor system that uses a conveyor belt to transport items. An enclosed fixture of the UV emission device may be arranged against a return surface of the conveyor belt, such as the underside of the belt, e.g., as the belt travels below the upper surface that transports items. The enclosed fixture may include one or more absorptive barriers near a periphery of the enclosed fixture, such as absorptive barriers comprising a material suitable to absorb UV energy. In addition, the absorptive barriers may create an emission seal against the return surface of the conveyor belt. The UV emission device may include one or more interlock switches that are engaged by the seal of the enclosed fixture. In some cases, responsive to disruption of the emission seal, the interlock switches may interrupt production of UV energy by the enclosed fixture, such as by disengaging a circuit of a UV emission element within the fixture. For example, the interlock switches may detect removal of the return surface from the absorptive barriers, and disengage power to the UV emission element.

In some implementations, the UV emission device may include one or more controller modules. The controller module may be configured to determine activity of the conveyor system, such as activity of a motor driving motion of the conveyor belt. The controller module may modify output of the enclosed fixture based on the determined conveyor activity. In some cases, the controller module may monitor the one or more interlock switches. Based on a condition of the interlock switches (e.g., engaged, interrupted), the controller module may provide a data signal indicating the output of the enclosed fixture. For example, if one or more of the interlock switches are disengaged, such as by disruption of the seal as described above, the controller module may provide display data that indicates an error condition, such as an alert describing the interrupted emission of the UV energy.

Ultraviolet ("UV") energy may have a disinfecting effect on surfaces. In some cases, the disinfecting effect of UV energy may be based on an electromagnetic wavelength of the UV energy, such as a range of the wavelength measured in nanometers. In addition, various usage guidelines may be associated with UV energy having various ranges of wavelength. For example, UV energy in a first wavelength range of about 200 nm to about 230 nm may kill or deactivate pathogens, when applied to a surface according to a first set of guidelines. In addition, UV energy in a second wavelength range of about 240 nm to about 260 nm may kill or deactivate pathogens, when applied to a surface according to a second set of guidelines. Furthermore, electromagnetic energy in a third wavelength range of about 400 nm to about 430 nm (e.g., visible light) may kill or deactivate some types of pathogens (e.g., bacteria, fungi), when applied to a surface according to a third set of guidelines. In some cases, guidelines associated with the example wavelength ranges may indicate particular intensities or duration of exposure to achieve a disinfecting effect.

In some cases, a disinfecting effect of UV energy may be based on an intensity of the UV energy, such as an intensity measured in microwatts ($\mu W$). In addition, a disinfecting effect of UV energy may be based on a duration of exposure to the UV energy, such as a duration measured in seconds. Applying UV energy to a moving surface, such as a surface of a conveyor system, may have a disinfecting effect that is based on a speed of the moving surface and an output of an emission element producing the UV energy. As a non-limiting example, a conveyor belt included in a checkout lane of a retail store environment may move at a speed of about 18 centimeters (cm) per second. An example UV emission device that produces UV energy at a wavelength of about 254 nm may be configured to direct about 2000 µW of UV energy at the moving surface of the conveyor belt. As an additional example, a UV emission device that implements one or more of the techniques described herein may be configured to direct UV energy at a moving conveyor belt surface for a conveyor system in which the UV emission device is installed. The example UV emission device may direct 5 µW of UV energy per $cm^2$ of the moving conveyor belt surface (e.g., 5 µJ of UV energy per $cm^2$ per second applied to the moving conveyor belt surface)

Pathogens may include microorganisms, bacteria, viruses, protozoa, prions, fungal spores, or other types of infectious agents. In some cases, UV energy may have a disinfecting effect on one or more types of pathogens, such as by rupturing a cell membrane, disrupting an DNA or RNA strand, or otherwise deactivating a function of a pathogen. In some cases, UV energy within a particular wavelength range may have a greater (or lesser) disinfecting effect on pathogens of a particular type. In the example UV emission device described above, directing 5 µW of UV energy per $cm^2$ to the moving conveyor belt surface may have a disinfecting effect that may deactivate some types of coronaviruses.

For convenience, and not by way of limitation, techniques related to a UV emission device are described herein in an example implementation of a conveyor belt within a retail checkout environment. However, other implementations are possible, such as a conveyor belt within a warehouse environment, a manufacturing environment, a mail-sorting environment, a package-distribution environment, an agricultural processing facility, or any environment or context in which a conveyor system may be included. In additional example implementations, a UV emission device may be configured for use with additional types of moving surfaces, such as a UV emission device that is configured for use with roller conveyors, segmented conveyors, manufacturing selection equipment (e.g., pick-and-place machines, agricultural sorting equipment) or other types of equipment that includes moving surfaces. In some implementations, a conveyor system may include a conveyor belt having a surface (or surfaces) comprising plastic, rubber, fabric, metal, glass, composite materials (e.g. fiberglass), or any other material or combination of materials suitable for a conveyor belt. In some cases, a conveyor belt may be constructed of a material that is resistant to UV energy, such as metal, glass, or other UV-resistant materials.

Referring now to the drawings, FIG. 1 is a diagram depicting an example of an environment including one or more conveyor systems, such as a conveyor environment 100. The conveyor environment 100 includes at least one conveyor system having a conveyor belt 110. As a non-limiting example, the conveyor belt 110 could be included in a conveyor system for a retail checkout station, such as a checkout station in a grocery store or a department store. The conveyor belt 110 may include one or more moving surfaces, such as a transport surface 112 and a return surface 114. The transport surface 112 may be arranged on an upper side of the conveyor belt 110, such as a surface that is configured to carry items that are placed on the belt 110. The return surface 114 may be arranged on a lower side of the conveyor belt 110, such as a surface that moves below the transport surface 112. In addition, the conveyor belt 110 may include one or more drums that are configured to propel the conveyor belt 110, e.g., across a surface of the example checkout station. For example, the conveyor belt 110 includes one or more rotor drums 105 that are configured to propel the transport surface 112 and the return surface 114 In some cases, the surfaces 112 and 114 are configured to move cyclically, such as a continuous (or nearly continuous) surface that is propelled by the rotor drums 105. In some cases, the rotor drums 105 may include an active drum, such as a drive drum, that includes one or more motor elements to propel the conveyor belt 110. In addition, the rotor drums 105 may include a passive drum, such as an idler drum, that includes is configured to rotate based on motion of the conveyor belt 110 (or another of the rotor drums 105). In some cases, the rotor drums 105 may have multiple sizes or shapes, such as a drive drum that has a larger size relative to an idler drum. In some implementations, the conveyor belt 110 may have one or more inclined surfaces, such as an incline for the return surface 114 (e.g., an incline against the different sizes of the rotor drums 105).

In some implementations, the conveyor environment 100 includes at least one UV emission device 120. The UV emission device 120 may include one or more of an enclosed fixture 125, in which a UV emission element 130 may be enclosed, or a controller module 140. The enclosed fixture 125 may be configured to fit against a moving surface of the conveyor belt 110, such as the return surface 114. In some cases, the enclosed fixture 125 may have a fitted configuration with respect to the conveyor belt 110. For example, the enclosed fixture 125 may have an incline that matches (or substantially matches) the incline of the return surface 114. Additionally or alternatively, the enclosed fixture 125 may have one or more adjustable components, such that the adjustable components fit against the incline of the return surface 114. In some cases, the fitted configuration of the enclosed fixture 125 may provide a sealed enclosure between the UV emission device 120 and the conveyor belt 110. In addition, the fitted configuration of the enclosed fixture 125 may enclose UV energy produced by the emission element 130, such that the return surface 114 receives UV energy within the sealed enclosure.

In FIG. 1, the enclosed fixture 125 includes the emission element 130, a power regulator 135, a housing 150, a reflector 137, and one or more absorptive barriers 160. In some cases, the enclosed fixture 125 includes one or more interlock switches, such as a switch 170. The emission element 130 may be capable of producing UV energy, such as electromagnetic energy having a wavelength in a range between about 100 nm to about 400 nm. The emission element 130 may include one or more energy emission elements, such as (without limitation) a low-pressure mercury lamp, an excimer lamp, a fluorescent lamp, a light-emitting diode ("LED") device, a pulsed xenon lamp, or any other energy emission element (or combination of elements) capable of producing UV energy. In addition, the power regulator 135 is configured to provide power (e.g., AC power, DC power) to the emission element 130. The power regulator 135 may include one or more of (without limitation) a ballast, an LED driver, an AC/DC transformer, or any other power regulation component (or combination of components) capable of regulating power provided to a UV emission element.

In some implementations, the emission element 130 may be arranged within the housing 150 such that UV energy produced by the emission element is directed towards the return surface 114. In some cases, the reflector 137 is arranged between the emission element 130 and the housing 150, such that UV energy outputted in a direction away from the return surface 114 is reflected by the reflector 137, e.g., towards the return surface 114. In some cases, the reflector 137 may be configured to direct reflected energy away from one or more of the housing 150 or the absorptive barriers 160.

In FIG. 1, the enclosed fixture 125 includes one or more of the absorptive barriers 160. The absorptive barriers 160 may be arranged at or near a periphery of the enclosed fixture 125, such as at or near one or more edges of the housing 150. The edges of the housing 150 may include one or more lateral edges or one or more longitudinal edges. In addition, the absorptive barriers 160 may comprise one or more materials that are suitable to absorb (or otherwise redirect) UV energy produced by the emission element 130. For example, and not by way of limitation, the absorptive barriers 160 may include one or more of fibrous material, foam, plastic, paper, or any other material (or combination of materials) suitable to absorb UV energy. In some cases, the absorptive barriers 160 may include one or more materials suitable to redirect UV energy. For example, the absorptive barriers 160 could include a fibrous material, which is absorptive, that is applied to a metal component, which is reflective. In addition, the absorptive barriers 160 may include one or more reflective or absorptive coatings, such as an absorptive or reflective coating applied to a component of the absorptive barriers 160.

In some implementations, the absorptive barriers 160 are configured to fit against the conveyor belt 110. For example, one or more of the absorptive barriers 160 may be fitted against the return surface 114. In some cases, the fitted configuration of the enclosed fixture 125 may apply pressure between the absorptive barriers 160 and the return surface 114. In addition, the absorptive barriers 160 may provide an emission seal between the enclosed fixture 125 and the conveyor belt 110. The emission seal may prevent UV energy produced by the emission element 130 from exiting the enclosed fixture 125. For example, a portion of UV energy that is not received by the return surface 114 (e.g., within the fitted configuration of the enclosed fixture 125) may be absorbed or otherwise redirected by the absorptive barriers 160. In some cases, the absorptive barriers 160 may have a pliability characteristic such that the emission seal is maintained during movement of the return surface 114. As a non-limiting example, the absorptive barriers 160 may include fibrous material, such as a brush component, that is capable of maintaining the emission seal while the return surface 114 moves past the fibrous material. In addition, the absorptive barriers may have a structural resistance characteristic such that pressure on the emission seal is maintained between the return surface 114 and one or more components of the enclosed fixture 125. As a non-limiting example, the absorptive barriers 160 may include plastic material, such as a semi-rigid flap component, that is capable of applying pressure between the return surface 114 and an interlock switch of the enclosed fixture 125. In some cases, the absorptive barriers 160 may include multiple absorptive materials. For example, the barriers 160 may include a first absorptive barrier and a second absorptive barrier. The first absorptive barrier may comprise fibrous material that is applied to the return surface 114. The fibrous material (e.g., bristles, felt, batting) may have one or more characteristics that create an emission seal that is flexible, such as to accommodate contours or movement of the return surface 114. The second absorptive barrier may comprise foam material that is applied to additional surfaces of the conveyor belt 110, such as a stationary frame in which the return surface 114 moves. The foam material (e.g., acrylic, silicone, vinyl) may have one or more characteristics that create an emission seal that is compressible, such as to accommodate rigid edges or surfaces of the conveyor system that includes the belt 110. Although the absorptive barriers 160 are described with regards to one or more of fibrous material or foam material, other materials may be used, such as rubber, plastics, metal (e.g., steel wool), or any other material (or combination of materials) that are capable of forming an emission seal against one or more surfaces of a conveyor system. In some cases, one or more of the absorptive barriers 160 may comprise polyethylene, such as ultra-high molecular weight polyethylene (e.g., "UHMWPE").

In some implementations, the enclosed fixture 125 includes one or more interlock switches, such as the switch 170. The interlock switches may be configured to identify a status of the enclosed fixture 125, such as whether the emission seal for the fixture 125 has a sealed status or an open status. In addition, the interlock switches may be configured to interrupt (or otherwise modify) output from the emission element 130 based on the status of the enclosed fixture 125. For instance, one or more interlock switches may be arranged at a periphery of the enclosed fixture 125. As a non-limiting example, at least one switch 170 may be placed at each corner of the housing 150. The switch 170 may be configured to determine whether the absorptive barriers 160 are providing the emission seal against the return surface 114. For example, the switch 170 may be configured to detect pressure that is applied to the absorptive barriers 160. Responsive to detecting a change in the emission seal, such as by detecting a release of pressure applied to the absorptive barriers 160, the switch 170 may interrupt power that is supplied to the emission element 130. For example, the switch 170 may be a normally open ("NO") switch that is configured to open a power circuit to one or more of the emission element 130 or the power regulator 135 if pressure on the barriers 160 is released.

Figure 2:
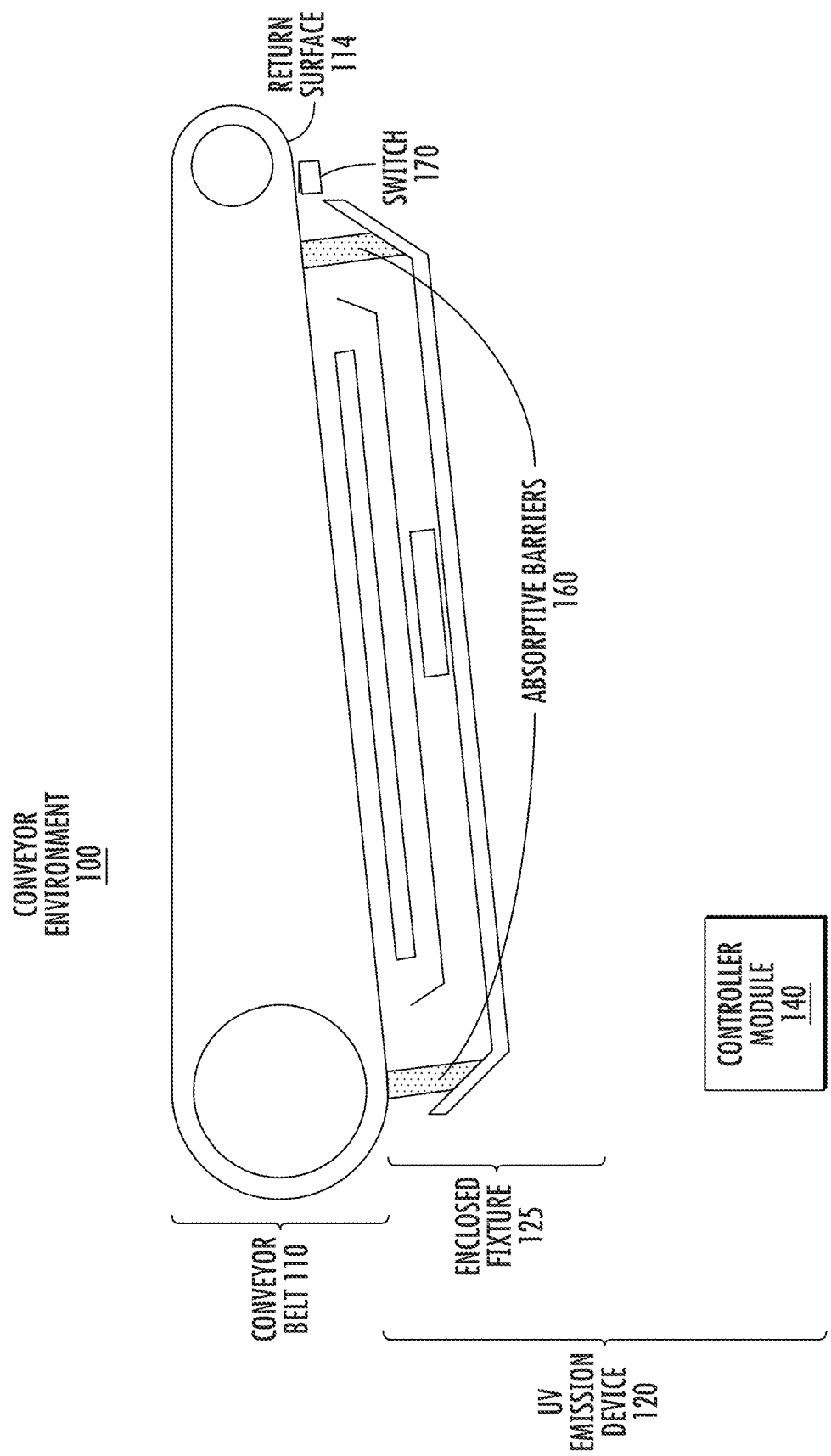
FIG. 2 is a block diagram depicting an example of a conveyor environment in which an enclosed fixture of a UV emission device has a fitted configuration with respect to a conveyor belt, according to certain implementations.

FIG. 2 is a diagram depicting an example of the conveyor environment 100 in which the enclosed fixture 125 has an example fitted configuration with respect to the conveyor belt 110. For illustrative purposes, and not by way of limitation, the fitted configuration depicted in FIG. 2 includes an emission seal formed between the absorptive barriers 160 and the return surface 114. For example, pressure may be applied between the absorptive barriers 160 and the return surface 114, such that UV energy produced by the emission element 130 is received by one or more of the return surface 114 or the absorptive barriers 160. In addition, the switch 170 may detect pressure applied to one or more of the return surface 114 or the absorptive barriers 160. For illustrative purposes, and not by way of limitation, FIG. 1 depicts a position of the enclosed fixture 125 in which the switch 170 is open, and FIG. 2 depicts a position of the enclosed fixture 125 in which the switch 170 is closed.

In some implementations, the controller module 140 of the UV emission device 120 may modify an output of the emission element 130. In some cases, the controller module 140 modifies the output of the emission element 130 based on activity of the conveyor belt 110. For example, the controller module 140 may receive a data signal indicating activity of one or more of the rotor drums 105. The data signal may indicate, for instance, that a drive drum is actively operating a motor, i.e. to propel movement of the conveyor belt 110. Responsive to an indication of motor activity, the controller module 140 may modify output of the emission element 130. For instance, responsive to determining that the rotor drums 105 are active (e.g., the conveyor belt 110 is moving), the controller module 140 may provide a data signal to the power regulator 135, such as an activation signal indicating increased output from the emission element 130. In some cases, the activation signal from the controller module 140 may indicate one or more of a power-on status, an increased intensity of output (e.g., exiting a dimmed state), modifying production of UV energy at a particular range of wavelengths, or any other suitable modification to output of the emission element 130. In addition, responsive to determining that the rotor drums 105 are inactive (e.g., the conveyor belt 110 is stopped), the controller module 140 may provide an additional data signal to the power regulator 135, such as a deactivation signal indicating decreased output from the emission element 130. In some cases, the deactivation signal from the controller module 140 may indicate one or more of a power-off status, a decreased intensity of output (e.g., entering a dimmed state), modifying production of UV energy at a particular range of wavelengths, or any other suitable modification to output of the emission element 130.

In some implementations, the controller module 140 may provide one or more data signals based on a status of interlock switches in the UV emission device 120. In some cases, the controller module 140 may receive a data signal indicating a status of the switch 170 (e.g., open status, closed status). In addition, the controller module 140 may provide a data signal indicating output of the emission element 130 based on the status of the switch 170. For example, based on a switch status signal indicating that the switch 170 is closed (e.g., pressure is applied between the return surface 114 and the absorptive barriers 160), the controller module 140 may provide a signal including display data describing activity of the emission element 130. In addition, based on a switch status signal indicating that the switch 170 is open (e.g., pressure is released from the absorptive barriers 160), the controller module 140 may provide a signal describing an error condition, such as display data indicating one or more of interrupted output by the emission element 130 or interruption of the emission seal for the enclosed fixture 125.

Figure 3:
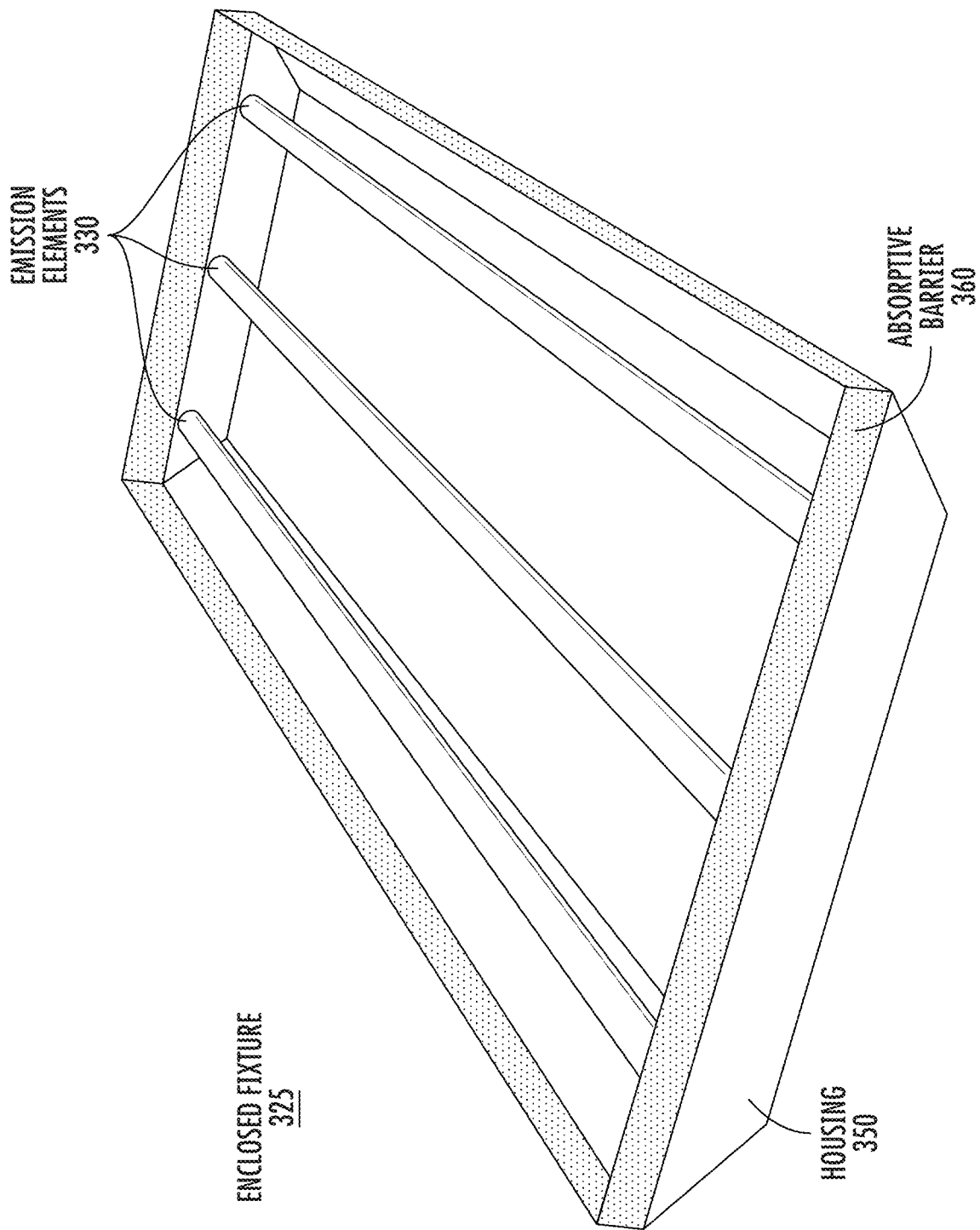
FIG. 3 is a view of an example enclosed fixture that includes emission elements, a housing, and an absorptive barrier, according to certain implementations.

In some implementations, a UV emission device may include one or more absorptive barriers that are arranged at or near a periphery of an enclosed fixture of the UV emission device. The absorptive barriers may be configured to perform an emission seal against an additional surface, such as a moving surface of a conveyor system against which the enclosed fixture is fitted. FIG. 3 depicts a view of an example enclosed fixture 325 that includes emission elements 330, a housing 350, and an absorptive barrier 360. In some cases, the enclosed fixture 325 may be included in a UV emission device, such as the UV emission device 120. The example enclosed fixture 325 includes one or more emission elements configured to produce UV energy, such as emission elements 330. In FIG. 3, the enclosed fixture 325 is depicted as including three emission elements 330 having an elongated shape, but other implementations are possible. For example, and not by way of limitation, an enclosed fixture could include one emission element or multiple emission elements. In addition, an enclosed fixture could include emission elements having an elongated shape, a curved shape, a flat shape (e.g., chip-on-board LED arrangements), or any other shape that is suitable to produce UV energy. In some cases, the example enclosed fixture 325 may be fitted against a conveyor system such that the emission elements 330 are arranged longitudinally with respect to a moving surface of the conveyor system, but other implementations are possible. For example, and not by way of limitation, an enclosed fixture could include one or more emission elements arranged horizontally, diagonally, as a parallel surface (e.g., chip-on-board LED arrangements), with curved elements, or with any other suitable configuration with respect to a moving surface of a conveyor system. In some implementations, an emission element that is arranged laterally with respect to movement of a conveyor belt surface (e.g., horizontal elements, diagonal elements, parallel surface elements) may improve a consistency of UV energy received by the moving surface. For example, a laterally-arranged emission element may provide a consistent amount of UV across the width of the moving surface, and can reduce a possibility of areas receiving lower exposure to the UV energy. In some cases, the enclosed fixture 325 may include one or more additional components, such as a reflector, a power regulator, an interlock switch, or any other additional suitable component.

In FIG. 3, the enclosed fixture 325 is depicted as including the absorptive barrier 360 at a perimeter of the housing 350. In some cases, the absorptive barrier 360 may be attached to the housing 350, such as via an adhesive or a mechanical attachment. In addition, the absorptive barrier 360 may be attached to an additional structure. The additional structure may include one or more of a barrier bracket that is configured to attach to the housing 350; a mounting bracket that is configured to attach to a conveyor system, such as a mounting bracket capable of fitting the enclosed fixture 325 against a conveyor belt; or another structure suitable for attaching one or more absorptive barriers. The enclosed fixture 325 may be fitted against a moving surface of a conveyor system, such as the return surface 114 of the conveyor belt 110. In addition, the absorptive barrier 360 may form an emission seal against the moving surface of the conveyor system. The emission seal formed by the absorptive barrier 360 may prevent UV energy produced by the emission elements 330 from exiting the fitted configuration of the enclosed fixture 325 against the moving surface of the conveyor system. In FIG. 3, the absorptive barrier 360 is depicted as a continuous material at the perimeter of the housing 350, but other implementations are possible. For example, an absorptive barrier may include multiple components, such as lateral barrier components comprised of a first material (e.g., brush components) and longitudinal barrier components comprised of a second material (e.g., foam components). In addition, an absorptive barrier may be arranged within a perimeter of an example housing, such as an absorptive barrier that is arranged within an edge of the example housing.

Figure 4:
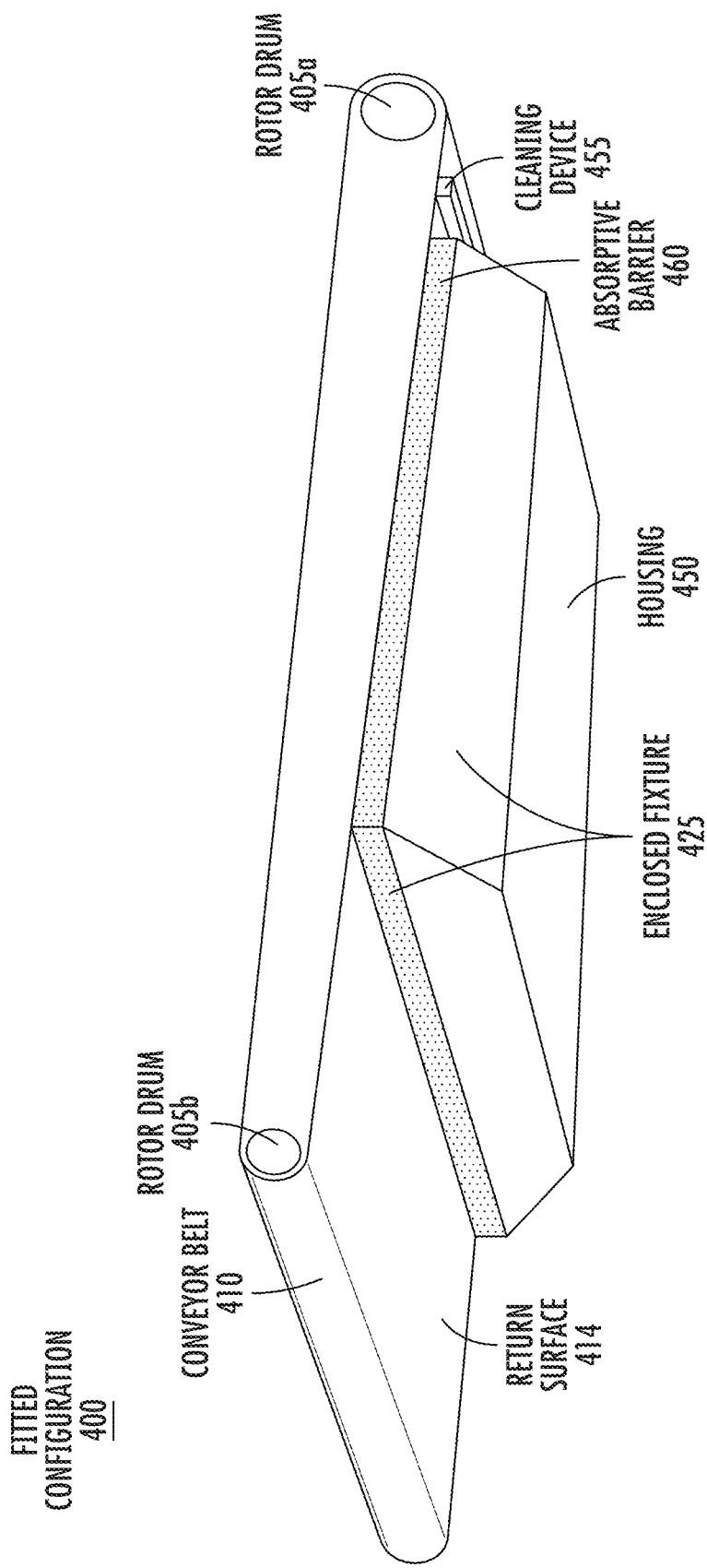
FIG. 4 is a view of an example fitted configuration between a conveyor belt 410 and an enclosed fixture, according to certain implementations.

In some implementations, a UV emission device may include an enclosed fixture capable of forming a fitted configuration against a moving surface of a conveyor system. In some cases, the fitted configuration may include an emission seal formed between the moving surface and the enclosed fixture. In addition, the emission seal may prevent UV energy produced within the enclosed fixture from exiting the fitted configuration. FIG. 4 depicts a view of an example fitted configuration 400 between a conveyor belt 410 and an enclosed fixture 425. The conveyor belt 410 may be included in a conveyor system, such as at a checkout station of a store. The enclosed fixture 425 may be included in a UV emission device, as described elsewhere herein. In FIG. 4, the conveyor belt 410 includes one or more of rotor drum 405a or rotor drum 405b (referred to collectively herein as rotor drums 405) and a return surface 414 that is arranged at an incline between the rotor drums 405. In some implementations, the enclosed fixture 425 (or an example UV emission device that includes the enclosed fixture 425) may include a cleaning device 455 that is in proximity to the conveyor belt 410. The cleaning device 455 may include one or more of a brush, a wiper blade (e.g., "squeegee"), a sponge, an air jet, or any other component or combination of components configured to clean a surface of the conveyor belt 410. In some cases, the cleaning device 455 may contact the return surface 414 of the conveyor belt 410. In addition, the cleaning device 455 may be arranged at a separation from the return surface 414, such that an output of the cleaning device 455 (e.g., a jet of air) may contact the return surface 414. In some cases, the cleaning device 455 (or an output of the cleaning device 455) may be arranged to remove from the conveyor belt 410 debris (e.g., crumbs, liquid) that might otherwise be introduced into the housing 450. For example, the cleaning device 455 (or an output thereof) may extend across the conveyor belt 410 at a location that is between an edge of the housing 450 and the rotor drum 405*a*. In some cases, the location of the cleaning device 455 may have a certain relation to a direction of movement of the conveyor belt 410. For instance, with respect to motion of the return surface 414 from rotor drum 405*a* to rotor drum 405*b* (e.g., along a bottom side of the conveyor belt 410), the cleaning device 455 may be located prior to the housing 450, such that debris can be removed from the return surface 414 at a point prior to the return surface 414 reaching the housing 450. In FIG. 4, the enclosed fixture 425 includes a housing 450 and an absorptive barrier 460 that is arranged around a perimeter of the housing 450. In FIG. 4, the depicted view of the fitted configuration 400 depicts a portion of the absorptive barrier 460, and additional portions may extend around the perimeter of the housing 450 (e.g., outside of the depicted view).

In FIG. 4, the fitted configuration 400 may include an emission seal formed between the absorptive barrier 460 and the return surface 414. The emission seal may prevent UV energy from exiting the fitted configuration 400, such as UV energy produced by one or more emission elements within the enclosed fixture 425. In addition, the fitted configuration 400 may direct UV energy towards the return surface 414 within the enclosed fixture 425. In some cases, the enclosed fixture 425 may include one or more additional components, such as a reflector, a power regulator, an interlock switch, or any other additional suitable component.

Figure 5:
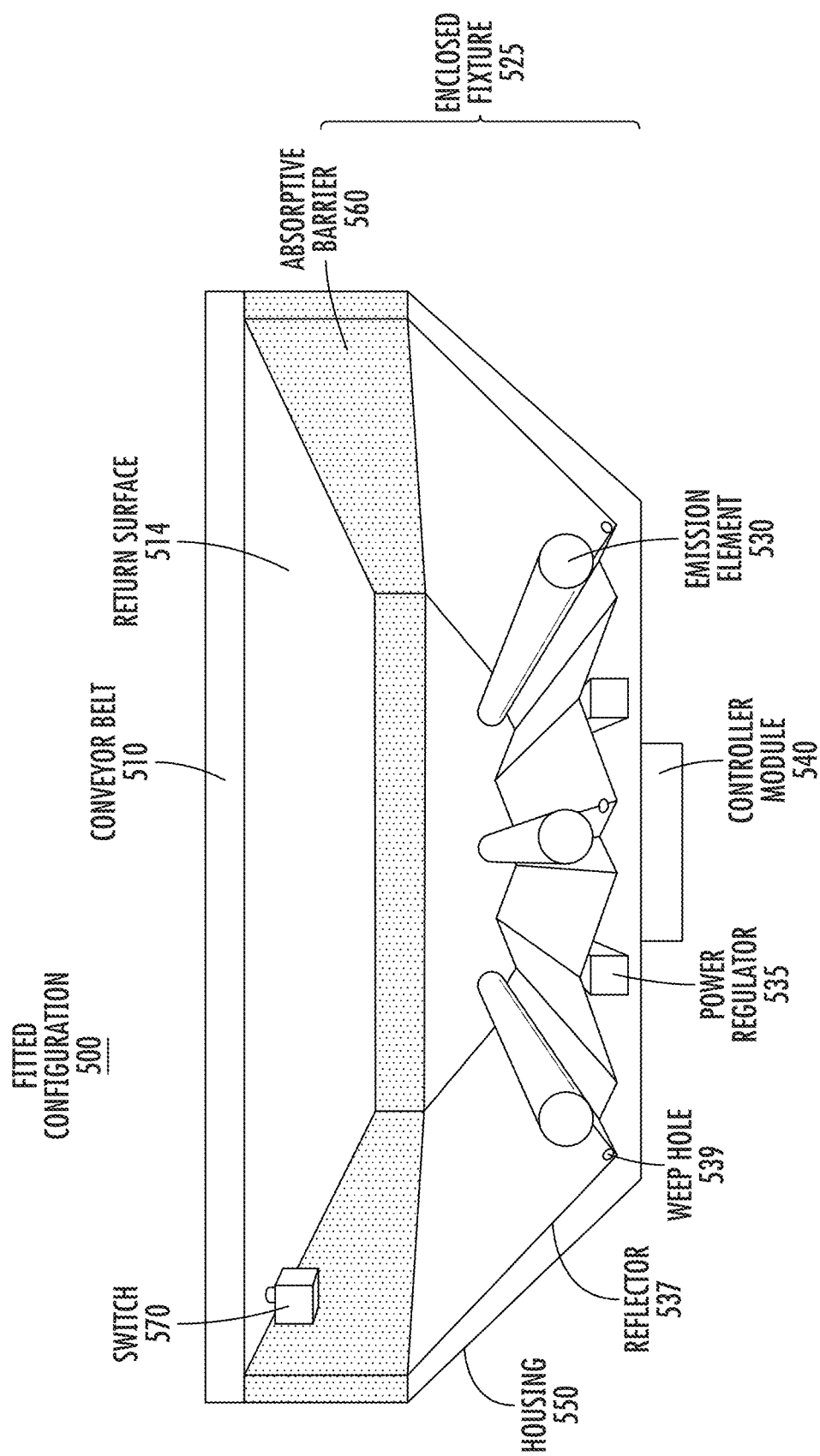
FIG. 5 is a section view of an example fitted configuration between a conveyor belt and an enclosed fixture, according to certain implementations.

In some implementations, a UV emission device may include one or more interlock switches that are configured to interrupt, or otherwise modify, output of one or more emission elements. For example, the interlock switches may be configured to determine a sealed status of an enclosed fixture of the UV emission device, such as whether the enclosed fixture has an emission seal with respect to a moving surface of a conveyor system. FIG. 5 depicts a section view of an example fitted configuration 500 between a conveyor belt 510 and an enclosed fixture 525. The conveyor belt 510 may be included in a conveyor system, such as at a checkout station of a store. The conveyor belt 510 may include a moving surface, such as a return surface 514. In some cases, the return surface 514 is arranged at an incline, such as between rotor drums of the conveyor belt 510.

In some implementations, the enclosed fixture 525 may be included in a UV emission device, as described elsewhere herein. In addition, the enclosed fixture 525 may include one or more of an absorptive barrier 560, a switch 570, the housing 550, or a reflector 537. In FIG. 5, the depicted view of the fitted configuration 500 depicts a portion of the absorptive barrier 560, and additional portions may extend around the perimeter of the housing 550 (e.g., outside of the depicted view). In some cases, the enclosed fixture 525 may include one or more emission elements configured to produce UV energy, such as an emission element 530, or one or more power regulators configured to regulate power provided to the emission element(s) 530, such as a power regulator 535. In some cases, the enclosed fixture 525 may include or be configured to communicate with a controller module, such as a controller module 540. In some implementations, one or more of the housing 550 or the controller module 540 may include an access area, such as an area by which an interior is accessible, e.g., for maintenance, programming modifications, cleaning, inspection, or other purposes. For example, the housing 550 may include a hinged portion that may be rotated (or otherwise displaced) to allow access to an interior of the housing 550, such as to replace an emission element. In addition, the controller module 540 may include a panel that may be removed (or otherwise displaced) to allow access to an interior of the controller module 540, such as an access interface within the module 540. In some cases, an access area of the housing 550 or controller module 540 may have an additional switch, such as an additional interlock switch configured to modify power to the emission element 530 responsive to determining that the access area is opened. For example, the additional interlock switch may be configured to interrupt power to the emission element 530 upon determining that the hinged portion of the housing 550 or the panel of the controller module 540 is opened.

In FIG. 5, the fitted configuration 500 may include an emission seal formed between the absorptive barrier 560 and the return surface 514. The emission seal may prevent UV energy, such as UV energy produced by the emission element 530, from exiting the fitted configuration 500. In addition, the fitted configuration 500 may direct UV energy towards the return surface 514 within the enclosed fixture 525. In some cases, UV energy may be directed towards a return surface 514 via the reflector 537. For example, the reflector 537 may include one or more surfaces having angles with respect to one or more of the emission elements within the enclosed fixture 525. In addition, the angled surfaces of the reflector 537 may reflect UV energy emitted by, for example, the emission element 530 towards the return surface 514. The reflector 537 includes flat (or nearly flat) surfaces having angles arranged around the example emission elements, but other configurations are possible, such as reflectors having curved surfaces or flat surfaces arranged at angles suitable to the shape of an emission element. In some implementations, one or more components of the enclosed fixture 525 may be arranged outside of the reflector 537 with respect to UV energy within the enclosed fixture 525. For example, the power regulator 535 may be arranged between the housing 550 and the reflector 537, such that UV energy emitted by the emission element 530 is reflected away from the power regulator 535 via the reflector 537. In addition, the controller module 540 may be arranged outside of the housing 550, such that the controller module 540 is outside of the emission seal formed by the absorptive barrier 560 and the return surface 514 In some cases, arranging components of the enclosed fixture 525 outside of the reflector 537 or the housing 550 may extend operating lifetimes of the components, such as by reducing or eliminating exposure of the components to UV energy produced within the enclosed fixture 525. In some implementations, the reflector 537 may include one or more weep holes, such as a weep hole 539, that are arranged to expel water or other liquid that enters the enclosed fixture 525 (e.g., via the conveyor belt 510). The weep hole 539 may be arranged at inflection points or inflection edges of the reflector 537, such as inflection points that are relatively low with respect to gravity. In some case, liquid that is received by the reflector 537 may follow a sloped surface of the reflector 537 towards the weep hole 539. In addition, the liquid may flow through the weep hole 539 to exit the reflector 537. In some cases, one or more additional weep holes may be arranged on the housing 550, such that liquid exiting the reflector is received by the additional weep hole of the housing 550 and exits the housing 550. In some cases, a first weep hole of the reflector 537 has a first location that is arranged with respect to a second location of a second weep hole of the housing 550. For example, the first location and second location may be arranged such that liquid exiting the first weep hole is received by the second weep hole via a path (e.g., a sloped surface, a pass-through) that routes the liquid away from other components of the enclosed fixture 525, such as the power regulator 535. In addition, the first location and second location may be arranged such that UV energy emitted by the emission element 530 is directed away from one or more of the first or second weep holes.

In some implementations, one or more interlock switches, such as the switch 570, may determine a status of the fitted configuration 500. For example, the switch 570 may be configured to determine pressure between the return surface 514 and the absorptive barrier 560. Responsive to a modification of pressure, e.g., an interruption or other change in the emission seal between the return surface 514 and the absorptive barrier 560, the switch 570 may change state, such as changing from a closed state to an open state. In some cases, the switch 570 is a normally open ("NO") switch that is configured to enter an open state when pressure is absent from an activator of the switch 570.

In addition, the switch 570 may be electrically connected to an electrical circuit that controls transmission of power to one or more power regulators or emission elements of the enclosed fixture 525. For example, the switch 570 may be configured such that power provided to the power regulator 535 or the emission element 530 is carried via the switch 570. In addition, the switch 570 may be configured to interact with a power circuit, such as interacting with a relay that is configured to carry power to the power regulator 535 or the emission element 530.

In some implementations, the switch 570 may be configured to interrupt power to one or more emission elements of the enclosed fixture 525 based on a modification of the fitted configuration 500. The power interruption may reduce or eliminate UV energy that is produced by emission elements within the enclosed fixture 525. In some cases, the switch 570 interrupts power to the emission elements responsive to a modification of the emission seal within the fitted configuration 500. For example, the switch 570 enters an open state responsive to insufficient pressure between the absorptive barrier 560 in the return surface 514, e.g., opening the emission seal. Based on the open state of the switch 570, power transmission to the emission elements may be interrupted, and production of UV energy within the enclosed fixture 525 may be stopped or reduced. In some cases, configuring one or more interlock switches to interrupt power to emission elements of the enclosed fixture 525 may improve safety of the UV emission device in which the fixture 525 is included, such as by reducing or eliminating production of UV energy when an emission seal of the fixture 525 is opened.

In some cases, the controller module 540 is configured to generate a data signal identifying a status of the fitted configuration 500. The data signal may identify an open status or an enclosed status for the fitted configuration 500. For example, the controller module 540 may receive one or more inputs indicating a state of the switch 570 (e.g., an open state, a closed state). Based on the one or more inputs, the controller module 540 may provide a data signal indicating the state of the switch 570. In addition, the data signal may indicate a condition of the emission seal in an area nearby the switch 570, such as an enclosed condition (e.g., the switch 570 is closed) or an open condition (e.g., the switch 570 is open). In some cases, the data signal provided by the controller module 540 may include configuration data to one or more output devices. For example, the data signal may configure a display device to display information describing the status of the fitted configuration 500. In addition, the data signal may configure an audio device to emit an audible alert, such as an alert indicating interruption of the emission seal in the area nearby the switch 570.

In some implementations, the controller module 540 may be configured to modify output of one or more of the emission elements within the enclosed fixture 525. In some cases, the output is modified based on activity of the conveyor belt 510. For example, the controller module 540 may receive a signal indicating activity of at least one motor element for a rotor drum that propels the conveyor belt 510. Responsive to an activity indicated by the signal, the controller module 540 may modify output of the emission element 530. For example, responsive to determining that the motor element is active (e.g., the conveyor belt 510 is moving), the controller module 540 may provide one or more data signals to the power regulator 535, such as a signal indicating increased output from the emission element 530. In addition, responsive to determining that the motor element is inactive (e.g., the conveyor belt 510 is stopped), the controller module 540 may provide one or more additional data signals to the power regulator 535, such as an additional signal indicating decreased output from the emission element 530.

In some cases, the controller module 540 may include one or more fans. The fans may be arranged to propel air into or out of the housing 550. In addition, the controller module 540 may be configured to control one or more of the fans, such as based on a temperature signal received from a thermal sensor within the enclosed fixture 525. For example, responsive to receiving a temperature signal indicating that an interior temperature of the enclosed fixture 525 is above a temperature threshold, the controller module 540 may generate a data signal activating one or more of the fans. In addition, the controller module 540 may modify output of one or more emission elements based on the temperature signal, such as by providing to the power regulator 535 a data signal indicating decreased output from the emission element 530. In some cases, a UV emission device with fans arranged within a controller module may provide an improved emission seal for the UV emission device. For example, airflows into or out of the example enclosed fixture 525 may be directed to a cavity between the housing 550 and the reflector 537, such as to where the power regulator 535 is arranged. In some implementations, the threshold temperature may establish a temperature for improved operation of the conveyor belt 510. For example, the controller module 540 may activate, or otherwise modify operation of, fans or other temperature control components responsive to determining that the temperature signal indicates that the interior temperature of the enclosed fixture 525 is outside of a targeted temperature range for operation of the conveyor belt 510. In some cases, the controller module 540 determines (or modifies) the threshold temperature responsive to an ambient temperature of an environment around the conveyor system of the belt 510. For instance, based on a received temperature data signal indicating an ambient temperature of a grocery store in which the conveyor belt 510 is located, the controller module 540 could modify the threshold temperature to indicate a range within 3 degrees C. of the ambient temperature of the grocery store. In some cases, maintaining a temperature within the enclosed fixture 525 that is within a targeted temperature range for conveyor belt operation improves user satisfaction with the conveyor belt 510, such as by avoiding melted groceries or reducing odors associated with heated material (e.g. dust, fibers) that is present on the conveyor belt 510.

Figure 6A:
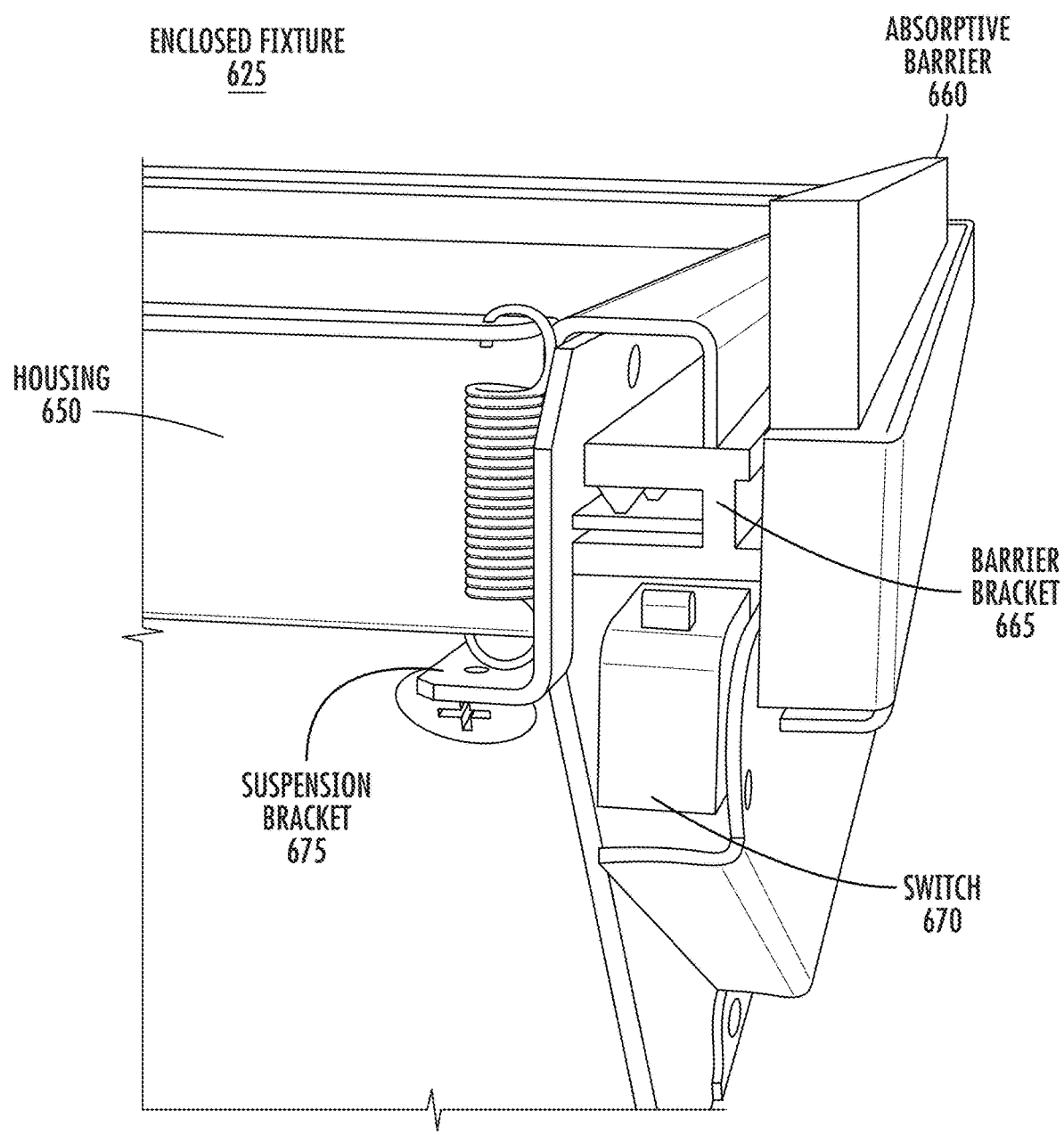
FIGS. 6a and 6b are views of an example enclosed fixture in which a switch is activated or deactivated via pressure applied to an absorptive barrier, according to certain implementations.
Figure 6B:
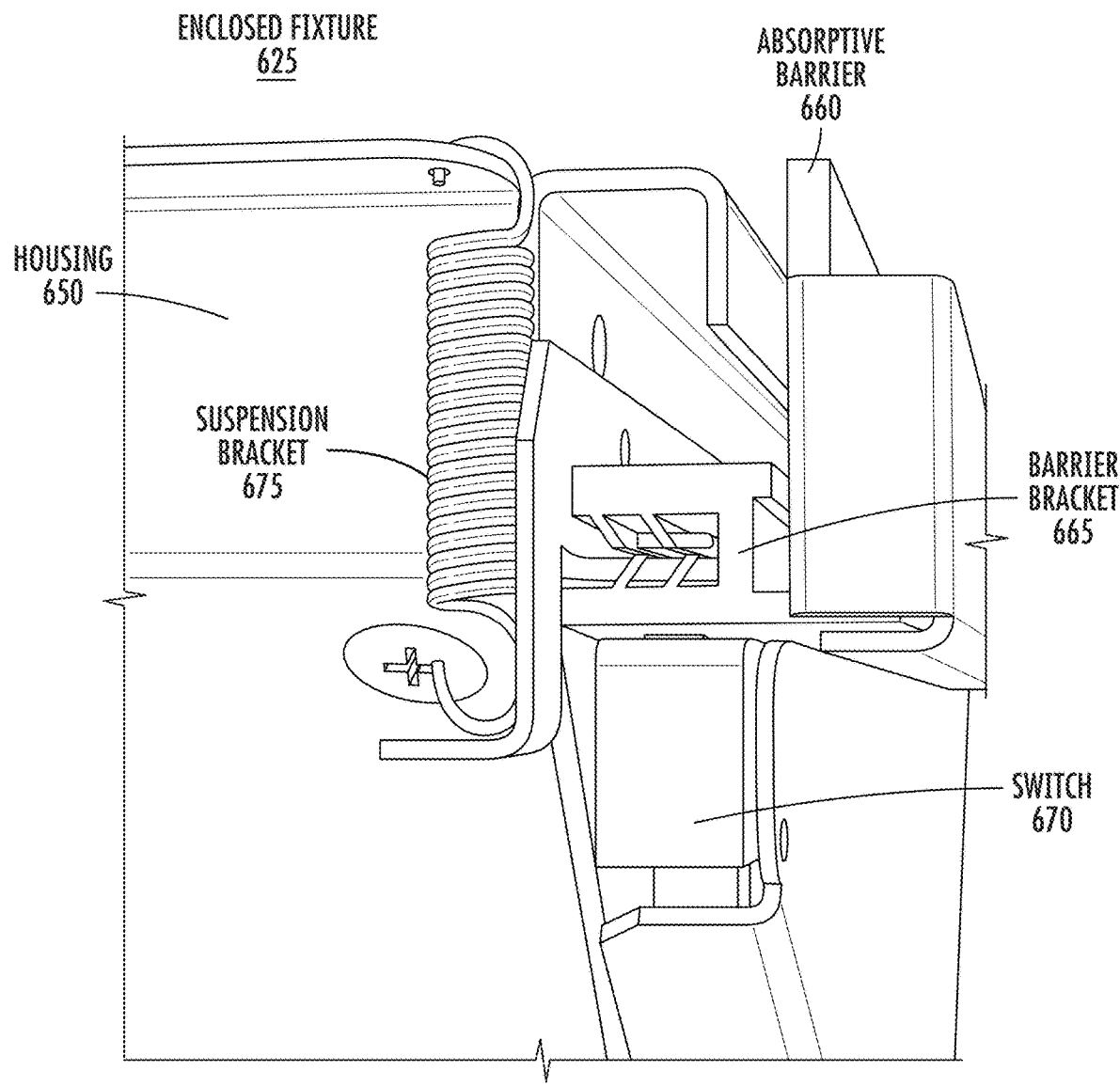

In some implementations, one or more interlock switches of a UV emission device may be activated or deactivated by pressure applied to an absorptive barrier in the UV emission device. For example, an interlock switch may be activated (e.g., closed) in response to receiving pressure from a barrier bracket to which the absorptive barrier is mounted. In addition, the interlock switch may be deactivated (e.g., opened) in response to pressure from the barrier bracket being released. FIG. 6a depicts a view of an example enclosed fixture 625 in which a switch 670 is deactivated via pressure applied to an absorptive barrier 660. FIG. 6b depicts an additional view of the enclosed fixture 625 in which the switch 670 is activated via pressure applied to the absorptive barrier 660. FIGS. 6a and 6b are collectively referred to herein as FIG. 6. The enclosed fixture 625 may be included in a UV emission device, as described elsewhere herein. In addition, the enclosed fixture 625 may include one or more of a housing 650, the switch 670, the absorptive barrier 660, a barrier bracket 665 to which the absorptive barrier 660 is mounted, or a suspension bracket 675 mounted to the housing 650. In some cases, the enclosed fixture 625 may be fitted against a moving surface of the conveyor system such that the absorptive barrier 660 forms an emission seal against the moving surface, as described elsewhere herein. In addition, the switch 670 may be electrically connected to an electrical circuit, such as an electrical circuit that supplies power to one or more power regulators or emission elements included in the enclosed fixture 625.

In FIG. 6, the barrier bracket 665 may be arranged along an edge of the housing 650. The barrier bracket 665 may support the absorptive barrier 660 along the edge, such that the absorptive barrier 660 extends along a perimeter of the housing 650. In addition, the barrier bracket 665 may be arranged in proximity to an activation element of the switch 670. For example, the barrier bracket 665 may be configured above the switch 670 such that pressure applied to the absorptive barrier 660 moves the barrier bracket 665 downwards (e.g., with respect to the housing 650) into contact with the activation element of the switch 670. In this example configuration, the switch 670 may be activated, via the barrier bracket 665, in response to pressure applied to the absorptive barrier 660. If the switch 670 is a normally open switch, activation via the barrier bracket 665 may place the switch 670 in a closed state. In addition, activation via the barrier bracket 665 may configure the switch 670 for a power transmission state, such as transmission of power by the electrical circuit that supplies power regulators or emission elements of the enclosed fixture 625.

In some implementations, the suspension bracket 675 may be arranged to interact with the barrier bracket 665. In addition, the suspension bracket 675 may include one or more components for generating force against the barrier bracket 665, such to propel the barrier bracket 665 in a direction towards a moving surface of the conveyor system. In FIG. 6, for instance, the suspension bracket 675 includes a flange that fits between multiple flanges of the barrier bracket 665. In addition, the suspension bracket 675 includes a biasing member, such as a spring, that is configured to generate force in a direction away from the activation element of the switch 670. In some cases, pressure that is applied to the absorptive barrier 660 (e.g., by a conveyor system surface against which the enclosed fixture 625 is fitted) may be applied to the flange of the suspension bracket 675, via the multiple flanges of the barrier bracket 665. In addition, the spring of the suspension bracket 675 may be extended by the pressure, such as depicted in FIG. 6b. Responsive to release of the pressure (e.g., interrupting an emission seal between the absorptive barrier 660 and the conveyor system surface), the spring may release, propelling the suspension bracket in a direction away from the activation element of the switch 670, such as depicted in FIG. 6a. In some cases, motion of the suspension bracket, e.g., away from the switch 670, applies pressure to the multiple flanges of the barrier bracket 665. FIG. 6a depicts a spring as an example of a biasing member, but other implementations are possible, such as a piston, an elastic member, or any other type of biasing member.

In the example configuration depicted in FIG. 6, pressure on the barrier bracket 665 may activate or deactivate the switch 670. As depicted in FIG. 6b, pressure on the barrier bracket 665 towards the switch 670, e.g., by a conveyor belt arranged against the enclosed fixture 625, may engage contact between the barrier bracket 665 and the activation element of the switch 670. In addition, as depicted in FIG. 6a, pressure on the barrier bracket 665 away from the switch 670, e.g., by the suspension bracket 675, may release contact between the barrier bracket 665 and the activation element of the switch 670. In some cases, the switch 670 may be deactivated in response to the contact being released. If the switch 670 is a normally open switch, deactivation may place the switch 670 in an open state. In addition, deactivation may configure the switch 670 for a power interruption state, such as interrupting power transmitted by the electrical circuit that supplies power regulators or emission elements of the enclosed fixture 625. In the power interruption state, production of UV energy by emission elements within the enclosed fixture 625 may be stopped or reduced. In some cases, configuring one or more interlock switches in the example configuration depicted in FIG. 6 may improve safety of a UV emission device in which the enclosed fixture 625 is included, such as by reducing or eliminating production of UV energy when an emission seal of the fixture 625 is opened.

Figure 7:
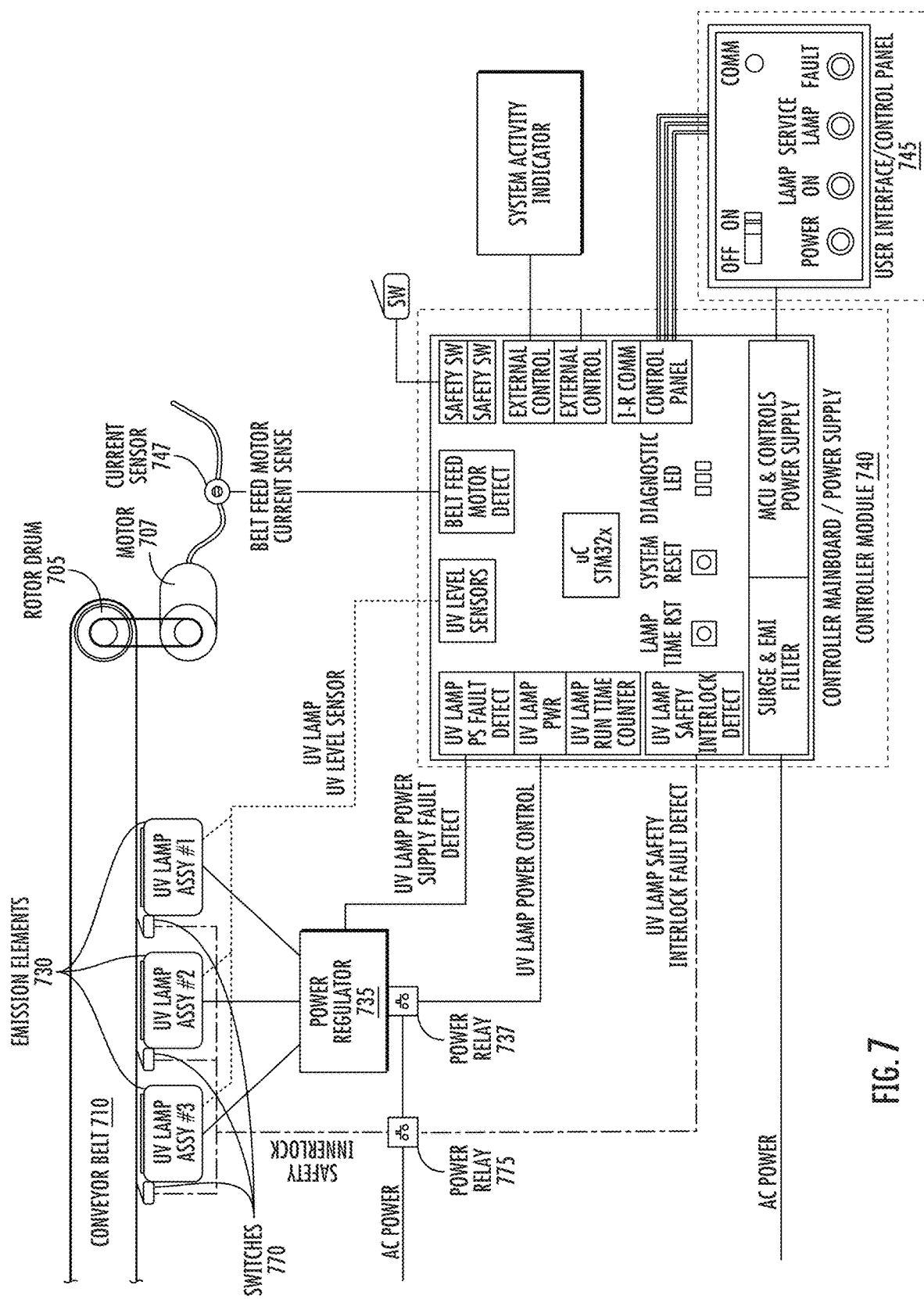
FIG. 7 is a block diagram depicting an example configuration of a controller module that may be included in a UV emission device, according to certain implementations.

FIG. 7 is a diagram depicting an example configuration of a controller module 740 that may be included in a UV emission device. In FIG. 7, one or more emission elements 730 may be configured to provide UV energy. The emission elements 730 may be arranged to direct UV energy towards a surface of a conveyor belt 710, such as within an enclosed fixture that has a fitted configuration against the conveyor belt 710. A power regulator 735 may provide power to the emission elements 730, such as power received via an AC power supply. In some cases, one or more of the power regulator 735 or the AC power supply are configured to provide surge protection. In addition, one or more interlock switches 770 are configured to identify a status of the fitted configuration. Based on the fitted configuration status, the interlock switches, the controller module 740, or an additional component of the example UV emission device may modify output of the emission elements 730.

In FIG. 7, one or more of the switches 770 may be electrically connected to a safety interlock of an AC power supply to the power regulator 735. For example, the switches 770 may be electrically connected to a power relay 775 that is configured to provide AC power to the power regulator 735. Responsive to one or more of the switches 770 having a particular state (e.g., an open state) indicating an interruption to the fitted configuration against the conveyor belt 710, the power relay 775 may modify state, such as from a closed state in which power is transmitted to an open state in which power is interrupted. Based on the modified state of the power relay 775, AC power to the power regulator 735 may be interrupted, and UV energy output by the emission elements 730 may be reduced or eliminated. In some cases, the controller module 740 may receive an input describing a status of the safety interlock or the power relay 775. For example, the controller module 740 may receive an interlock signal at an input for a UV lamp safety interlock fault detect. Responsive to the interlock signal, the controller module 740 may provide one or more output signals, such as a display signal provided at an external control output. The display signal may be received by one or more output devices, such as by a system activity indicator device or a fault indicator that is included in a user interface/control panel 745 ("UI panel 745").

As depicted in FIG. 7, there may be an electrical connection between the switches 770 and the power relay 775. However, other implementations are possible. For example, one or more interlock switches may be electrically connected (e.g., "in-line") to a power circuit that transmits power to one or more power regulators of the emission elements, such that deactivation (or activation) of the interlock switch interrupts the transmission of power. In addition, a controller module may receive an input from one or more interlock switches, such that the controller module is configured to interrupt power to an emission element (e.g., via a control signal to a power regulator) responsive to deactivation (or activation) of the interlock switch.

In some implementations, the controller module 740 may provide a power control signal for one or more of the power regulator 735 or the emission elements 730. For example, the controller module 740 may provide a control signal at an output for a UV lamp power control. The control signal may be received by the power regulator 735. In some cases, the control signal is received via a power relay 737 that is configured to provide AC power to the power regulator 735. Responsive to the control signal, the power regulator 735 (or the power relay 737) may modify output of one or more of the emission elements 730. In some cases, modifying output of the emission elements 730 may include one or more of increasing output, decreasing output, powering an emission element on or off, modifying a wavelength range for UV energy produced by an emission element, or any other suitable modification to UV energy produced by the emission elements 730.

In some cases, the controller module 740 may provide the power control signal responsive to an input signal received via the UI panel 745. For example, responsive to an input that indicates a selected disinfection effect with respect to a particular pathogen, the controller module 740 may provide a power control signal that modifies output of the emission elements 730 to produce UV energy having a wavelength and intensity suitable to increase (or decrease) a disinfection effect with respect to the particular pathogen. As a non-limiting example, if an input signal is received indicating a selected disinfection effect for bacteria associated with foodborne illnesses, the controller module 740 could generate a power control signal for the emission elements 730 to produce UV energy at a wavelength and intensity that increases deactivation of the indicated bacteria. In some cases, operation of one or more additional components may be modified responsive to the input indicating the selected disinfection effect. For example, the controller module 740 may generate an output signal that indicates a decrease (or increase) in speed of the motor 707. In addition, the controller module 740 may provide the output signal to the motor 707 (or a system capable of controlling the motor 707), such that the conveyor belt 710 move more slowly (or quickly) with respect to the emission elements 730, receiving a higher (or lower) intensity of UV energy.

In some implementations, the power relay 737 may modify state responsive to an input from the controller module 740. In addition, the power relay 775 may modify state responsive to an input from one or more of the switches 775. For example, the power relay 775 may change state independent of operations by the controller module 740. As a non-limiting example, if operations of the controller module 740 are interrupted (e.g., power failure, firmware malfunction), the power relay 775 may continue to receive inputs from the switches 770, and may modify state, e.g., interrupting power to the power regulator 735, responsive to activation of one of the switches 770. In some cases, a UV emission device that includes a power relay that may modify state responsive to an input from an interlock switch may have improved reliability, such as by interrupting power to an emission element independently of a controller module. In addition, a UV emission device that includes a first power relay that modifies state responsive to an input from an interlock and a second switch power relay that modifies state responsive to an input from a controller may have further improved reliability, such as by enabling redundant power relay control of power to an emission element. For example, in the event of a failure (e.g., welded contacts, broken input pins) in one of either the first power relay or the second power relay, power to the emission element may be controlled via the remaining power relay.

In some cases, the controller module 740 may receive one or more inputs describing a status of the emission elements 730. For example, the controller module 740 may receive a UV level signal at an input for a UV lamp UV level sensor. In some cases, a UV level sensor may be configured to detect a level of UV energy that is received from a UV emission device. Based on a UV level signal, the controller module 740 may determine an output of a UV emission element, or determine if the output of the UV emission element is within a threshold level of UV energy. For example, if a covering of the UV emission device becomes dirty, the UV level sensor may provide a signal that indicates a reduced output of the UV emission device. The controller module 740 may determine that the UV output is below the threshold level. In some cases, responsive to determining that the UV output is below the threshold level, the controller module 740 may modify power provided to the UV emission device, such as by powering off the UV emission device. In some cases, the controller module 740 may provide data indicating that the UV emission device has reduced output, such as a maintenance alert signal provided to a building maintenance system. In addition, the controller module 740 may receive a lamp fault signal at an input for a UV lamp power supply fault detect. Responsive to receiving the lamp fault signal, the controller module 740 may modify an output of one or more of the emission elements 730. In addition, responsive to receiving the lamp fault signal, the controller module 740 may provide one or more output signals, such as an output signal to a fault indicator that is included in the UI panel 745.

In some implementations, the controller module 740 may modify output of one or more of the emission elements 730 based on a motor activity signal from a motor 707 associated with a rotor drum 705. For example, the controller module 740 may receive a motor activity signal at an input for a belt feed motor detect. In FIG. 7, the motor activity signal may be generated via one or more components configured for current sensing, such as a current sensor 747 that is configured to detect current supplied to the motor 707. In some implementations, the current sensor 747 may be installed on or near a power supply connection of the motor 707 without disrupting operations of the motor 707, such as in a retrofit configuration of a UV emission device that includes the current sensor 747. In some cases, the current sensor 747 provides a belt feed motor current sense signal to the controller module 740, such as via the belt feed motor detect input.

In some implementations, the controller module 740 may receive data signals from one or more additional components, such as components of a UV emission device or a conveyor system in which the UV emission device is installed. For example, the controller module 740 may receive an input from an optical sensor of the conveyor system that is configured to detect motion of the conveyor belt 710, a proximity sensor that is configured to detect a presence of items on the conveyor belt 710, a power component that is configured to provide power to the conveyor system, or any other suitable component (or combination of components) of a conveyor system. In addition, the controller module 740 may receive an input from a motion-sensing component of the UV emission device that is configured to detect activity of one or more of the conveyor belt 710, the motor 707, or an additional motor of a conveyor system that includes the conveyor belt 710. The controller module 740 may receive an activity signal (such as a motor activity signal) that indicates one or more of motion of the conveyor belt 710, motor activity of the motor 707 driving the conveyor belt 710, or motion of an additional component of the conveyor system that includes the conveyor belt 701. In some cases, the motion-sensing component may be configured to detect one or more frequencies associated with the motor 707, such as an accelerometer that detects a vibration of the motor 707, a microphone that detects a sound of the motor 707, or another motion-sensing device configured to detect frequencies. One or more of the controller module 740 or the motion-sensing component may be configured to filter out frequencies or vibrations that are associated with other sources (e.g., vibrations of a fan, vibrations of voices). In some cases, the motion-sensing component may be configured to detect motion of the conveyor belt 710, such as an optical sensor configured to detect motion of the conveyor belt 710. Furthermore, the motion-sensing component may be configured to detect motion of or another moveable component of the conveyor system, such as a rotational encoder configured to detect motion of a shaft or other component of the motor 707. In addition, the controller module 740 may receive an input from an optical sensor of the UV emission device that is configured to detect motion of the conveyor belt 710, a temperature sensor, a UV energy sensor, a fan, or any other suitable component (or combination of components) of a UV emission device.

In some cases, the controller module 740 may include or be configured to communicate with one or more communication components, such as an antenna or a modem for wired or wireless communications. In addition, the controller module 740 may be configured to communicate with one or more additional computing systems, such as a building maintenance system that monitors performance of operational systems for building (e.g., lighting systems, security systems, fire suppression systems). In some cases, the controller module 740 may be configured to provide data to a building maintenance system, such as a signal indicating operational data or a maintenance alert signal. Operational data may include data describing functions of the UV emission device or a conveyor system with which the UV emission device is installed. The controller module 740 may generate operational data based on additional data, such as an operational counter indicating a quantity of power cycles of the UV emission element, time data indicating hours of movement of the belt 710, or any additional data that describes functions of the UV emission device or the conveyor system. A maintenance alert signal may include data describing a failure, or a potential failure, of one or more components in the UV emission device or the conveyor system. The controller module 740 may provide the maintenance alert signal responsive to receiving a system operational signal, such as a UV level signal, a temperature signal, a signal indicating a component fault, or any other signal indicating a system operating condition. In addition, the system operational signal may include a signal generated by the controller module 740, such as a system operational signal generated responsive to determining that an operational counter has exceeded (or has another relationship to) an operational threshold value.

Figure 8:
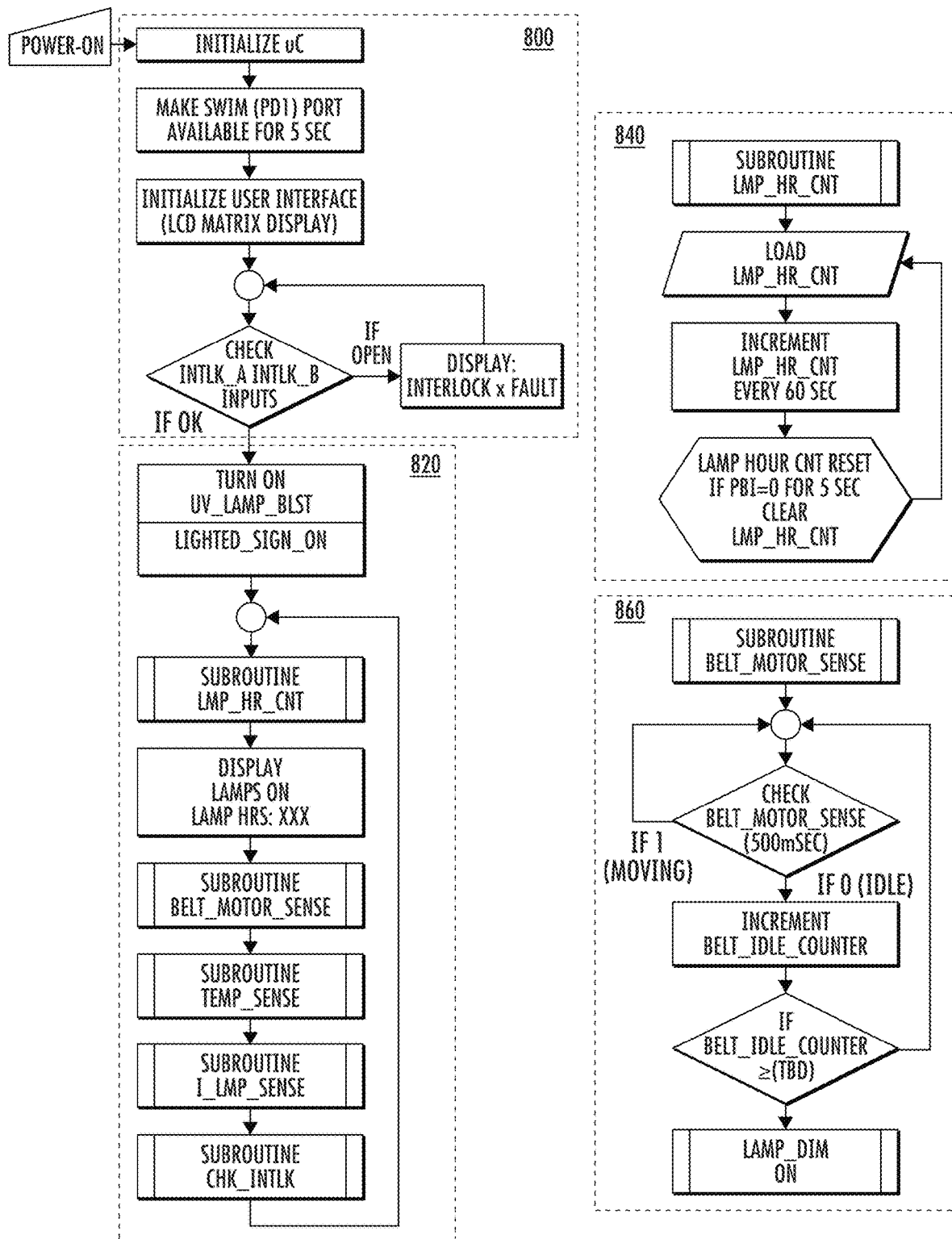
FIG. 8 includes flow charts depicting examples of one or more processes for a controller module of a UV emission device, according to certain implementations.
Figure 9:
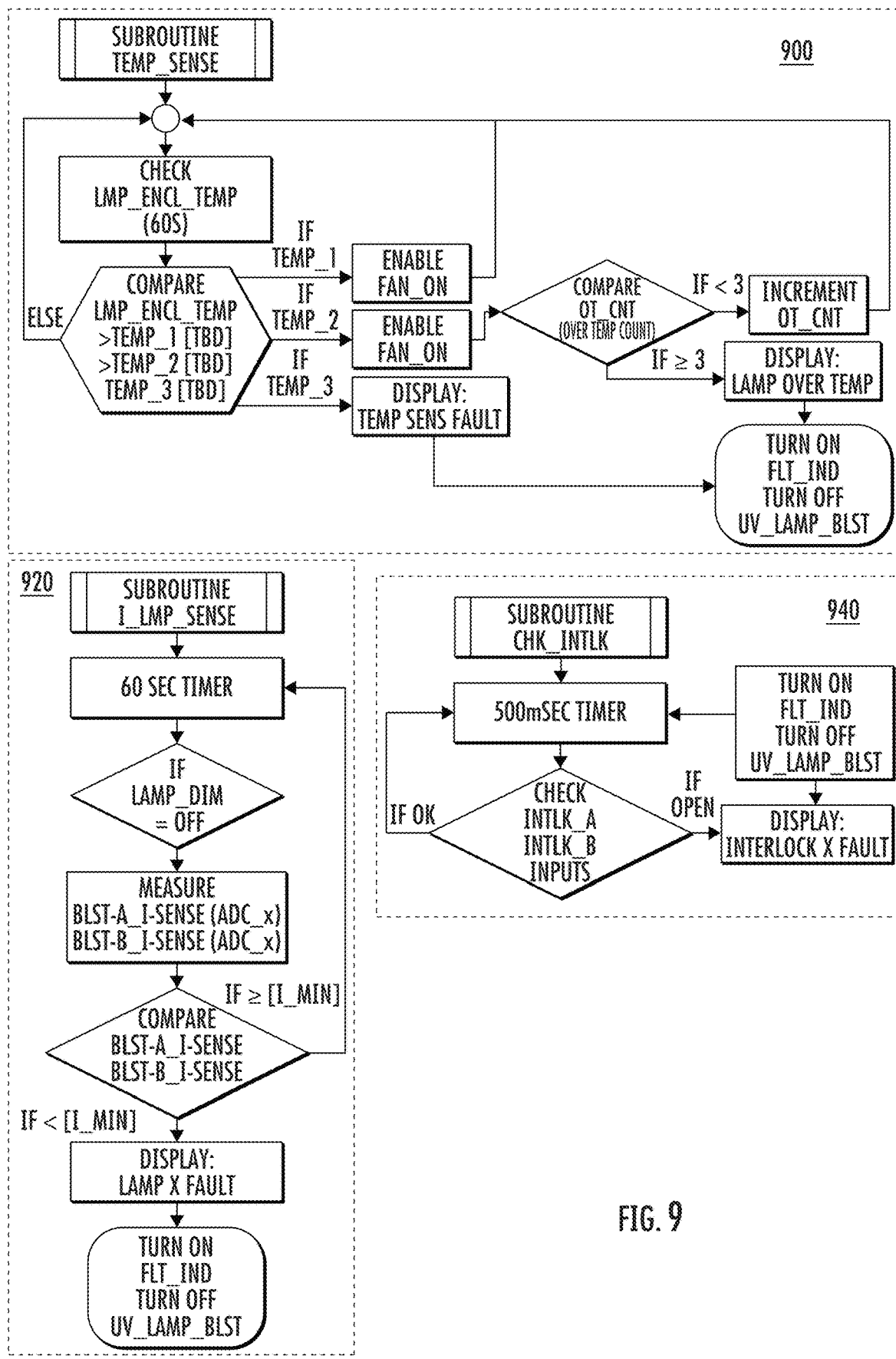
FIG. 9 includes flow charts depicting examples of one or more processes for a controller module of a UV emission device, according to certain implementations.

FIG. 8 and FIG. 9 include flowcharts depicting examples of one or more processes for a controller module of a UV emission device. In some implementations, such as described in regards to FIGS. 1-7, a computing device executing a controller module of a UV emission device implements operations described in one or more of FIG. 8 or 9, by executing suitable program code. For illustrative purposes the processes described in regards to FIGS. 8 and 9 are described with reference to the examples depicted in FIGS. 1-7. Other implementations, however, are possible.

In some implementations, one or more operations included in the processes 800, 820, 840, 860, 900, 920, or 940 may be performed by a controller module included in a UV emission device, such as one or more of the controller modules 140, 540, or 740. Example implementations of a controller module may include one or more of a microprocessor, an application-specific integrated circuit ("ASIC"), a field-programmable gate array ("FPGA"), or other suitable processing device. The controller module can include any number of processing devices, including one.

Process 800 includes one or more example operations for initializing a controller module included in a UV emission device. For example, the process 800 may include one or more operations related to initialization of a microcontroller of the controller module, checking for inputs pending on one or more input ports of the controller module, initializing one or more user interface devices that are in communication with the controller module, and determining a status of one or more interlock switches that are in communication with the controller module.

In some implementations, the controller module implementing the process 800 may identify interlock signals received as inputs from one or more interlock switches. If the interlock signals indicate that one or more interlock switches are disengaged (e.g., in an open state), the controller module may provide a data signal indicating an interlock fault, such as error information displayed via one or more output devices. For example, the controller module 740 may identify one or more interlock signals received from one or more of the switches 770. Responsive to determining that the interlock signals indicate that one or more of the switches 770 are disengaged from the conveyor belt 710, the controller 740 may provide a display data signal to one or more of the UI panel 745 or an additional system activity indicator.

In some cases, the controller module implementing the process 800 may continue to check the interlock signals received from the interlock switches. If the interlock signals continue to indicate disengagement of the interlock switches, the controller module may discontinue (or otherwise not perform) one or more operations related to providing power to an emission element in the UV emission device. For example, the controller module may loop between operations for checking the interlock signals and providing a data signal indicating interlock fault. In some cases, the controller module may avoid implementing operations that are not included in process 800 until the interlock signals indicate that the interlock switches are engaged (e.g., in a closed state).

Process 820 includes one or more examples of operations, performed by the controller module, related to modifying UV energy produced by one or more emission elements included in the UV emission device. For example, the process 820 may include one or more operations related to powering on a lamp ballast or other power regulation device for an emission element, powering on a lighted sign or other output device, providing display data indicating operational information of an emission element, or performing one or more subroutines. In some cases, the controller module may perform one or more operations of process 820 responsive to determining that the interlock signals (e.g., received in regards to process 800) indicate that the interlock switches are engaged. In some implementations, the controller module may repeat a sequence of one or more operations in the process 820, such as an operational loop that includes one or more of the subroutines of the process 820.

Process 840 includes one or more examples of operations, performed by the controller module, for modifying a counter indicating operational time, such as a counter indicating operational time of one or more emission elements of the UV emission device. For example, the process 840 may include one or more operations related to entering or leaving a subroutine indicated by the process 820, determining a data element describing an operational counter, incrementing the operational counter (e.g., incrementing every 60 seconds), or checking a reset signal for the operational counter. In some implementations, the operational counter may indicate a number of minutes (or other suitable time period) elapsed during operation of one or more emission elements, such as the emission elements 730. In addition, the operational counter (or an additional operational counter) may indicate a number of switching events elapsed with regards to operation of emission elements, such as a quantity of power cycles (e.g., turning emission elements on or off) or a quantity of dimming cycles (e.g., reducing power to an emission element). In some cases, the controller module may return to process 820 upon completion of operations included in the process 840. In some cases, the controller module may repeat one or more operations in the process 840.

In some implementations, the UV emission device may determine maintenance data based on the process 840 or the operational counter. For instance, based on the operational counter indicating a particular quantity of operational time for an emission element, the UV emission device may provide a data signal to display a "Replace Lamp" message. In some cases, a UV emission device that implements the process 840 may provide improved maintenance data, and an efficiency of the UV emission device may be improved, such as by replacing components that are approaching an end of functional lifespan. In some cases, a controller, such as the controller module 740, may provide data indicating that operational counter has reached a threshold value. For example, responsive to determining that the operational counter has reached an operational threshold value (e.g., 1000 hours of operation), the controller may provide a maintenance alert signal provided to a building maintenance system or to a user interface component (e.g., a message provided for a display device, an alert indicator on a control panel).

Process 860 includes one or more examples of operations, performed by the controller module, for modifying output of one or more emission elements of the UV emission device based on a motor activity signal. For example, the process 860 may include one or more operations related to entering or leaving a subroutine indicated by the process 820 or checking a motor activity signal, such as the belt feed motor current sense signal described in regards to FIG. 7. If the motor activity signal indicates that a conveyor belt (e.g., against which the UV emission device is fitted) is moving, the controller module may repeat one or more operations, such as checking the motor activity signal again. If the motor activity signal indicates that the conveyor belt is idle, the controller module may perform one or more additional operations of the process 860, such as incrementing a belt idle counter, comparing the incremented belt idle counter to an activity threshold, or dimming one or more emission elements of the UV emission device. For example, if the controller module 740 determines that the motor activity signal received from the current sense component indicates that the motor 707 has been idle for amount of time equal to or greater than an activity threshold time (e.g., 20 seconds, 2 minutes), the controller module 740 may send a control signal to the power regulator 735 indicating a reduction in output of one or more the emission elements 730. In some cases, the controller module may return to the process 820 upon completion of operations included in the process 860. In some cases, the controller module may repeat one or more operations in the process 860. In some cases, a UV emission device that implements the process 860 may perform with improved energy efficiency, such as by dimming emission elements while a conveyor belt is idle. In addition, a UV emission device that implements the process 860 may perform for an improved period of time, such as by extending an operational lifespan of one or more components of the UV emission device, such as a lifespan of an emission element or a reflector. Furthermore, a UV emission device that implements the process 860 may improve operation of a conveyor system in which the UV emission device is installed, such as by extending an operational lifespan of a conveyor belt of the conveyor system. In addition, a UV emission device that implements the process 860 may eliminate or reduce an operational delay upon startup. For example, emission elements that are dimmed may return to full operation more quickly, e.g., upon opening a checkout lane in which the UV emission device is installed, as compared to emission elements that are powered down.

In some implementations, a UV emission device that includes a current sense component, such as the current sensor 747, may be configured to execute the process 860. In addition, the UV emission device with the current sense component may be applied to a conveyor system that is already installed, such as a retrofit configuration of the UV emission device. In the example retrofit configuration, the UV emission device determines activity of the conveyor system via one or more of the current sense component or the process 860, without disrupting operation of the conveyor system as already installed. For example, the UV emission device may determine motor activity of the conveyor system via the current sense component, without modifying operations of a motor of the conveyor system. In some cases, the example UV emission device (e.g., having the current sensor 747 and configured with the process 860) may be applied to a conveyor system in the example retrofit configuration with reduced financial costs and time expenditure, as compared to an installation that does not include the retrofit configuration.

Process 900 includes one or more examples of operations, performed by the controller module, for determining a temperature within an enclosed fixture of the UV emission device. For example, the process 900 may include one or more operations related to entering or leaving a subroutine indicated by the process 820, checking a temperature signal, or comparing the temperature signal to one or more temperature thresholds. In some cases, the temperature signal is received from one or more temperature sensors included within the enclosed fixture. If the temperature signal is below the one or more the temperature thresholds, the controller module may repeat one or more operations, such as checking the temperature signal again. If the temperature signal indicates that the temperature within the enclosed fixture is above at least one of the temperature thresholds, the controller module may perform one or more additional operations of the process 900, such as turning on at least one fan if the temperature signal exceeds a first temperature threshold; turning on at least one additional fan if the temperature signal exceeds a second temperature threshold; providing display data indicating a temperature fault, such as error information displayed via one or more output devices, if the temperature signal exceeds a third temperature threshold; or modifying an output (e.g., dimming, powering off) of one or more emission elements if the temperature signal exceeds the third temperature threshold. In some cases, the process 900 includes additional operations related to modifying a counter indicating over-temperature time, such as comparing an over-temperature counter to an over-temperature threshold, incrementing the over-temperature counter, or providing additional display data (e.g., additional error information) indicating the over-temperature time. In some cases, the process 900 includes one or more operations related to modifying an output (e.g., dimming, powering off) of one or more emission elements based on the temperature signal. For example, if the controller module 740 determines that the temperature signal is equal to or greater than one or more temperature thresholds, the controller module 740 may send a control signal to the power regulator 735 indicating a reduction in output of one or more of the emission elements 730. In addition, the controller module 740 may send a data signal to one or more of the UI panel 745 or an additional system activity indicator, such as display data indicating a temperature fault. In some cases, the controller module may return to the process 820 upon completion of operations included in the process 900. In some cases, the controller module may repeat one or more operations in the process 900.

Process 920 includes one or more examples of operations, performed by the controller module, for identifying faulty operation of one or more emission elements included in the UV emission device. For example, the process 920 may include one or more operations related to entering or leaving a subroutine indicated by the process 820, incrementing a timer (e.g., a 60 second wait period), determining if an emission element is dimmed, checking a current sense signal for the emission element, or comparing the current sense signal to a current sense threshold. If the current sense signal is greater than or equal to the current sense threshold, the controller module may repeat one or more operations, such as resetting the timer or checking the current sense signal again. If the current sense signal is less than the current sense threshold (e.g., the emission element is drawing insufficient current and is not dimmed), the controller module may perform one or more additional operations of the process 920, such as providing display data indicating an emission element fault, such as error information displayed via one or more output devices. In some cases, the process 920 includes one or more operations related to modifying an output of the emission elements based on the current sense signal. For example, if the controller module 740 determines that the current sense signal for a particular one of the emission elements 730 is below the current sense threshold, the controller module 740 may send a control signal to the power regulator 730 indicating a powering off of the particular emission element. In addition, the controller module 740 may send a data signal to one or more of the UI panel 745 or an additional system activity indicator, such as display data indicating a fault with the particular emission element. In some implementations, the controller module repeats one or more operations of the process 920 for each emission element included in the UV emission device, such as by comparing a respective current sense signal for each of the emission elements to the current sense threshold. In some cases, the controller module may return to the process 820 upon completion of operations included in the process 920.

Process 940 includes one or more examples of operations, performed by the controller module, for checking the interlock signals received from the one or more interlock switches included in the UV emission device. In some cases, the controller module may modify operation of one or more emission elements in the UV emission device based on the interlock signals. For example, the process 940 may include one or more operations related to entering or leaving a subroutine indicated by the process 820, incrementing a timer (e.g., a 500 ms wait period), or checking one or more interlock signals received from the interlock switches. If the interlock signals (e.g., for all emission elements in the UV emission device) indicate that the interlock switches are engaged, the controller module may repeat one or more operations, such as resetting the timer or checking the interlock signals again. If one or more of the interlock signals indicate that an associated interlock switch is disengaged (e.g., an emission seal of the UV emission device is opened) the controller module may perform one or more additional operations of the process 940, such as modifying operation of one or more emission elements or providing display data indicating an interlock fault, such as error information displayed via one or more output devices. For example, if the controller module 740 determines that an interlock signal indicates that one or more of the interlock switches 770 is disengaged, the controller module 740 may send a control signal to the power regulator 735 indicating a powering off of the emission elements 730. In some cases, the power regulator 735 receives the control signal in addition to a power interruption provided by one or more of the power relays 775 or 737. In addition, the controller module 740 may send a data signal to one or more of the UI panel 745 or an additional system activity indicator, such as display data indicating an interlock fault. In some cases, the controller module may return to the process 820 upon completion of operations included in the process 940. In some cases, the controller module may repeat one or more operations in the process 940.

In some implementations, a UV emission device is applied to a conveyor system in a retrofit configuration. For example, a grocery store or retail store may include multiple conveyor systems that have an existing configuration in the store, such as a set of checkout lanes. One or more UV emission devices may be installed in the checkout lanes by retrofitting one or more of the conveyor systems to have a UV emission device applied to a conveyor belt of the conveyor system. In some cases, a retrofit configuration of one or more UV emission devices may improve installation efficiency, such as by reducing time and financial costs related to installation of the UV emission devices. In addition, the retrofit configuration of the UV emission devices may reduce negative impact on conveyor systems in which the UV emission devices are installed, such as by reducing alterations or accidental damages caused to the conveyor systems.

Figure 10A:
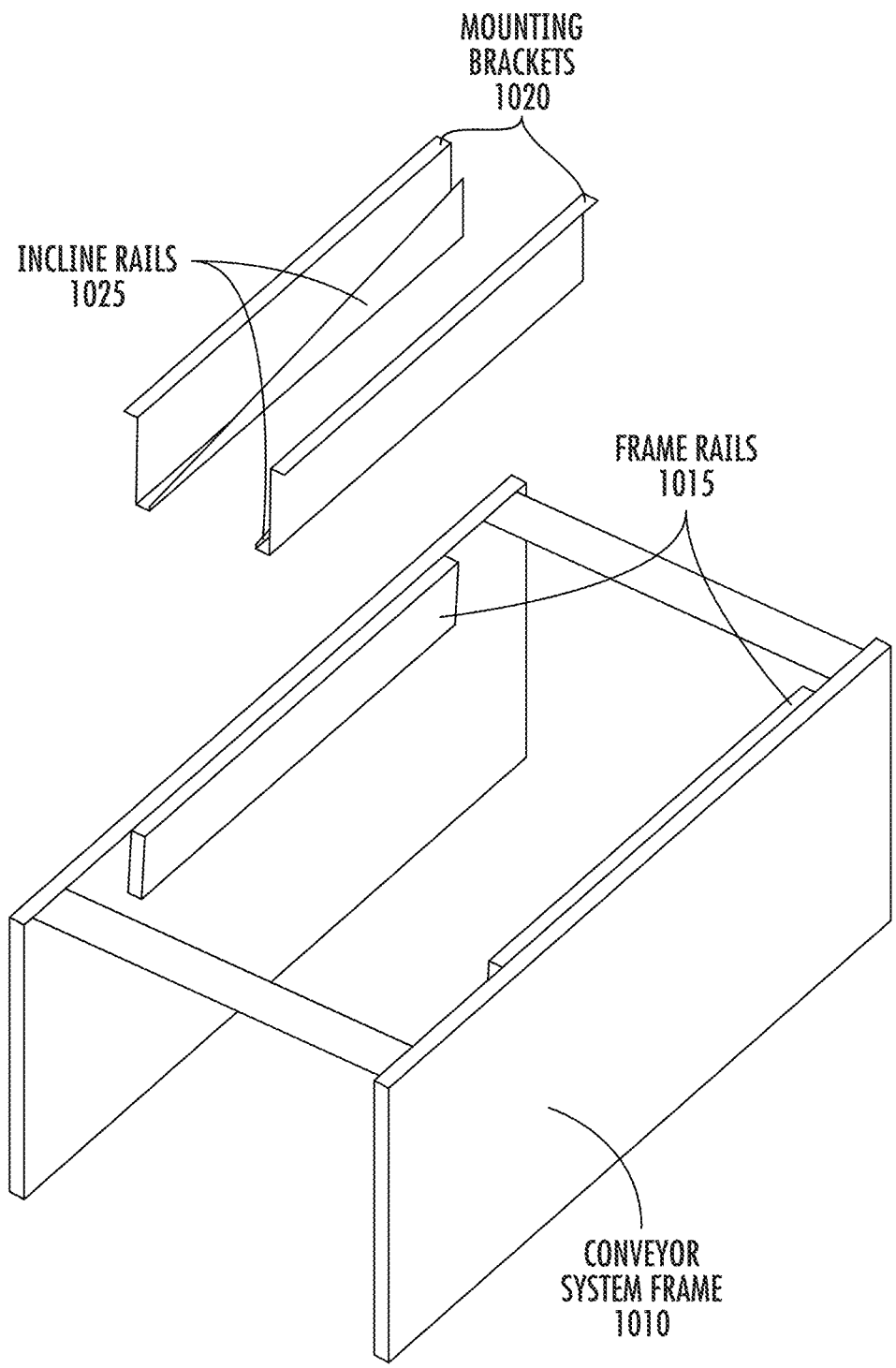
FIGS. 10a-10f are views of an example set of mounting brackets that may be applied to a conveyor system in a retrofit configuration, according to certain implementations.
Figure 10B:
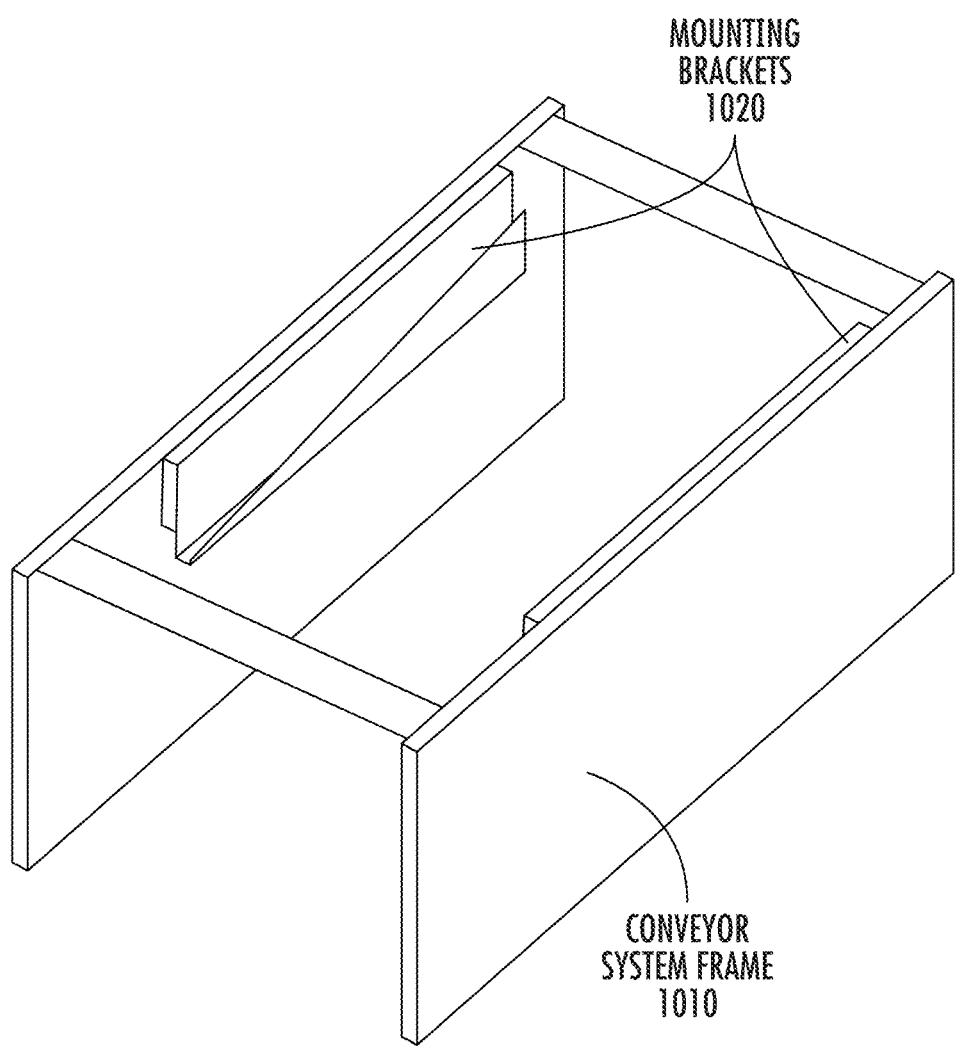
Figure 10C:
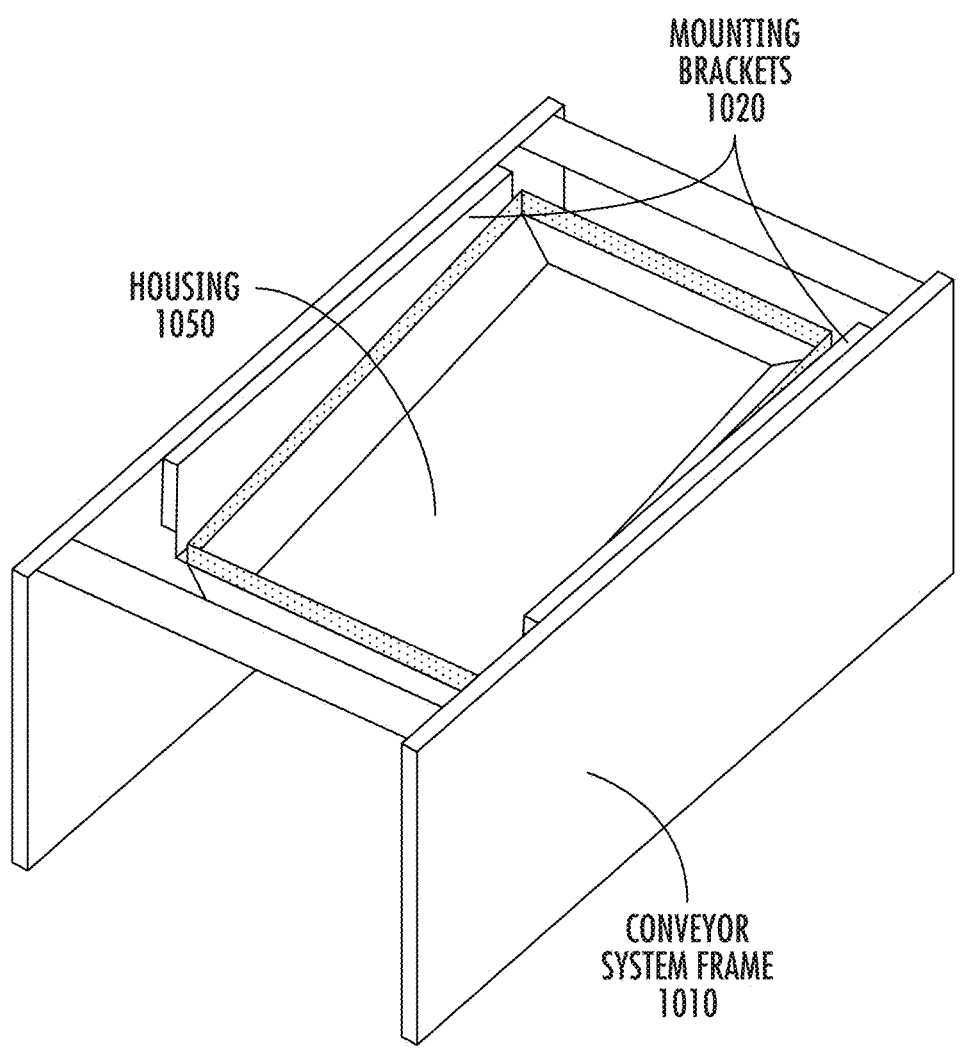
Figure 10D:
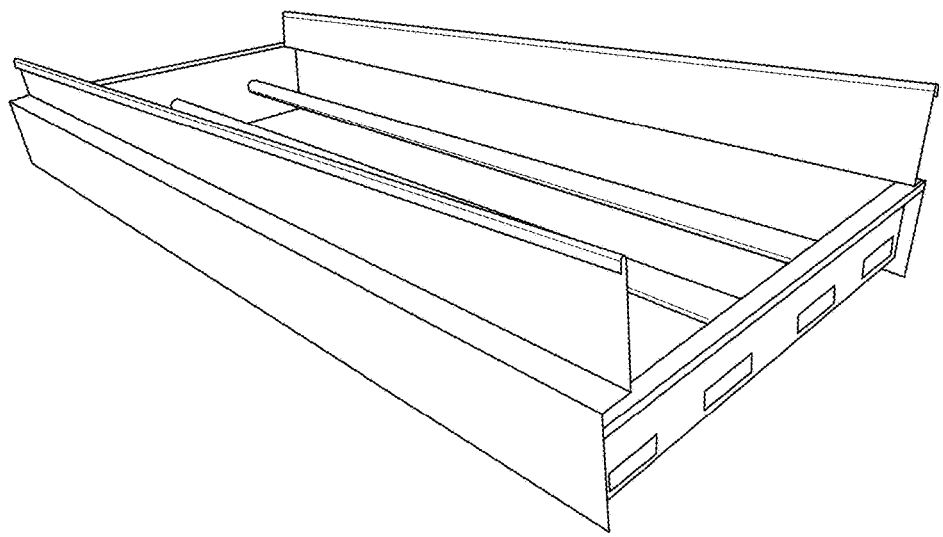
Figure 10E:
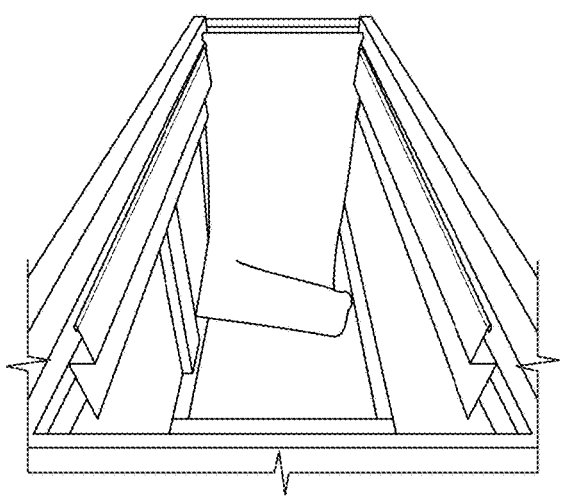
Figure 10F:
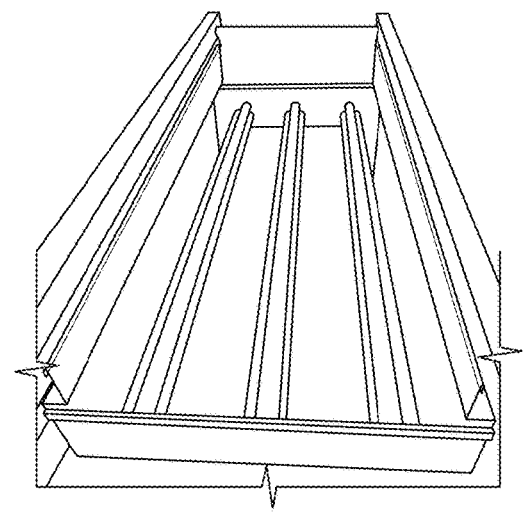

In some retrofit configurations, a UV emission device may be installed in a conveyor system via one or more mounting techniques. The mounting techniques may position an enclosed fixture of the UV emission device in a fitted configuration against a conveyor belt of the conveyor system. FIG. 10a depicts a view of an example set of mounting brackets 1020 that may be applied to a frame 1010 of a conveyor system in a retrofit configuration. FIG. 10b depicts an additional view of the set of mounting brackets 1020 installed on the conveyor system frame 1010. FIG. 10c depicts an additional view of a housing 1050 positioned on the mounting brackets 1020. FIG. 10d depicts an example of a mounting bracket in which an example of an enclosed fixture may be installed. FIG. 10e depicts an example of a mounting bracket that is installed in an example of a conveyor system frame. FIG. 10f depicts the example mounting bracket by which an example of an enclosed fixture is installed in the example conveyor system frame. FIGS. 10a, 10b, 10c, 10d, 10e, and 10f are collectively referred to herein as FIG. 10. The conveyor system frame 1010 may be included in a conveyor system that has an existing configuration, such as a checkout lane in a store. In some cases, the housing 1050 is included in an enclosed fixture of a UV emission device that is installed on the example conveyor system via the example retrofit configuration.

In some cases, the mounting brackets 1020 may include one or more components to adjust a position of the housing 1050. For example, the mounting brackets 1020 may include one or more incline rails 1025. The incline rails 1025 may be formed by one or more features of the mounting brackets 1020, such as extruded plastic or sheet metal folded to form a support rail. In some cases, a shape of the incline rails 1025 may match (or substantially match) a shape of a conveyor belt included in the example conveyor system. For example, a slope of the incline rails 1025 may be similar to a slope of a return surface on the conveyor belt. In some cases, an emission seal between the enclosed fixture and the conveyor belt may be improved by a similarity of slope between the incline rails 1025 and the return surface.

In some implementations, the mounting brackets 1020 may be fitted onto one or more existing features of the conveyor system in which the UV emission device is installed. For example, the conveyor system frame 1010 may include one or more frame rails 1015. In some cases, the frame rails 1015 are existing structural features of the frame 1010 (e.g., wooden or metal support structures). In the example retrofit configuration of the UV emission device, the mounting brackets 1020 may attach to the frame rails 1015. For example, the mounting brackets 1020 may have one or more features configured to fit onto one or more surfaces of the frame rails 1015. FIG. 10b depicts a non-limiting retrofit configuration in which the mounting brackets 1020 are attached to a longitudinal surface of the frame rails 1015. In some cases, the mounting brackets 1020 may include one or more mechanical fasteners (e.g., screws, nails, latches) that attach to the frame rails 1015 or other features of the frame 1010. In addition, the mounting brackets 1020 may attach to the frame rails 1015 without mechanical fasteners, such as a pressure fit between the frame rails 1015 and one or more features of the mounting brackets 1020.

FIG. 10c depicts a non-limiting retrofit configuration in which the housing 1050 is positioned on the mounting brackets 1020. The mounting brackets 1020 may be installed on the frame rails 1015, as described in regards to FIG. 10b. In addition, the housing 1050 is positioned on the mounting brackets 1020 such that the enclosed fixture of the housing 1050 is fitted against a moving surface of the conveyor system, e.g., a return surface of the conveyor belt. In the example retrofit configuration of FIG. 10c, the position of the housing 1050 may be adjusted on the mounting brackets 1020, such as by sliding the housing 1050 along the incline rails 1025. In some cases, the position of the housing 1050 or the corresponding enclosed fixture on the mounting brackets 1020 may form an emission seal against the moving surface of the conveyor system. In addition, adjusting the position of the housing 1050 on the mounting brackets 1020 may adjust the emission seal. For example, if the housing 1050 is positioned more closely to the conveyor belt, such as by adjusting the housing's position on the incline rails 1025, pressure may be increased between the conveyor belt and an absorptive barrier of the corresponding enclosed fixture. In some cases, one or more interlock switches of the corresponding enclosed fixture may be activated or deactivated via adjustments to the pressure between the conveyor belt and the absorptive barrier.

In some cases, the incline rails 1025 may be configured to position an enclosed fixture in a fitted configuration against a conveyor system. For example, the incline rails 1025 may be configured to support the housing 1050 in a position that brings the enclosed fixture into contact with a conveyor belt of the conveyor system. In addition, the position of the housing 1050 (or the corresponding enclosed fixture) may be adjusted on the mounting brackets 1020, such as by adjusting the housing 1050 along the incline rails 1025. In some implementations, the mounting brackets 1020 may improve a retrofit configuration of the example UV emission device, such as by positioning the housing 1050 on the conveyor system frame 1010 without additional modifications or damage to the frame 1010 (e.g., drilling holes, soldering brackets). In addition, an emission seal between the enclosed fixture and the conveyor belt may be improved by the incline rails 1025 or other features of the mounting brackets 1020, such as by improving adjustability of the enclosed fixture with respect to the conveyor belt.

Figure 11A:
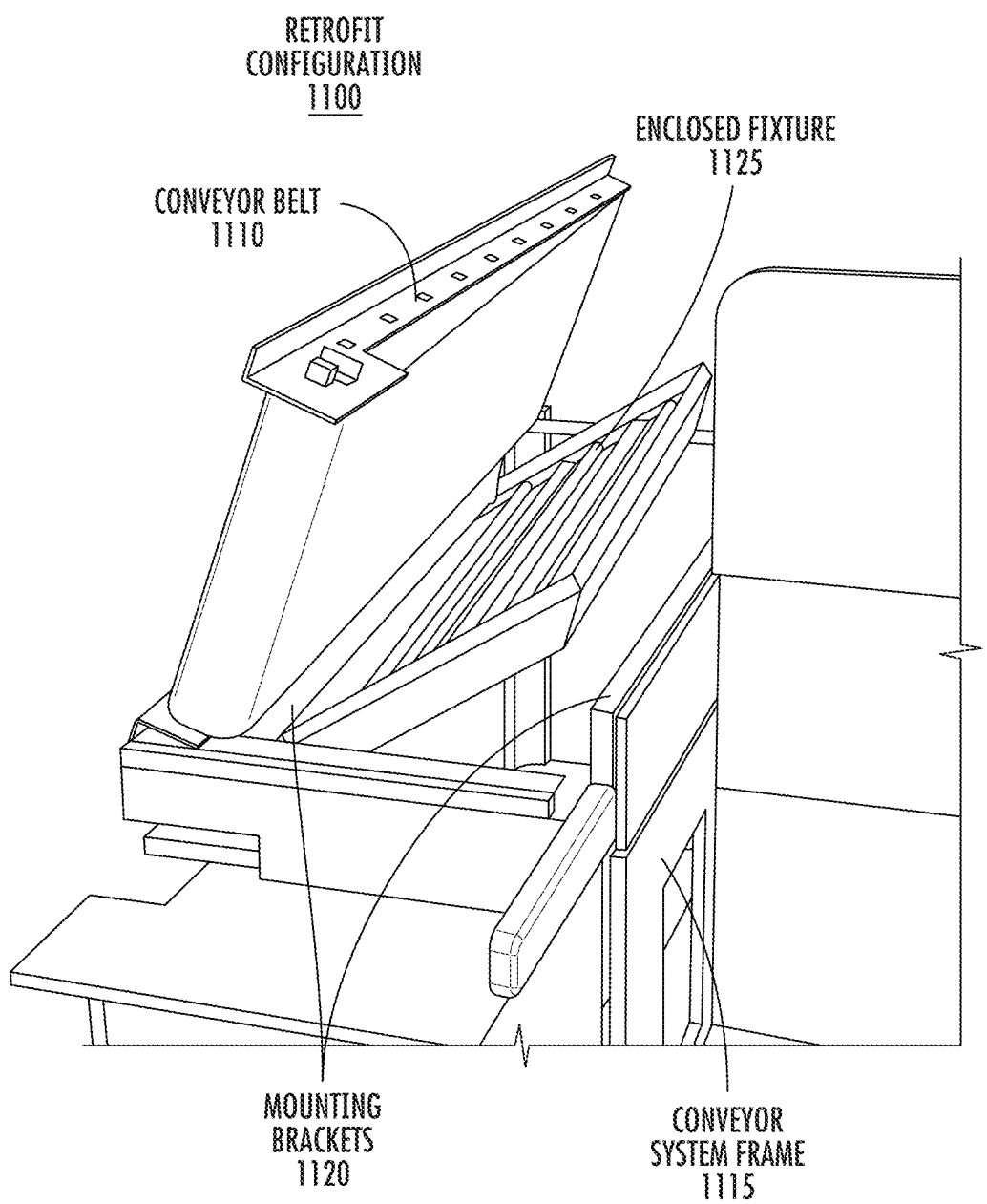
FIGS. 11a-11c are views of an example retrofit configuration in which a conveyor belt is repositioned with respect to a frame, according to certain implementations.
Figure 11B:
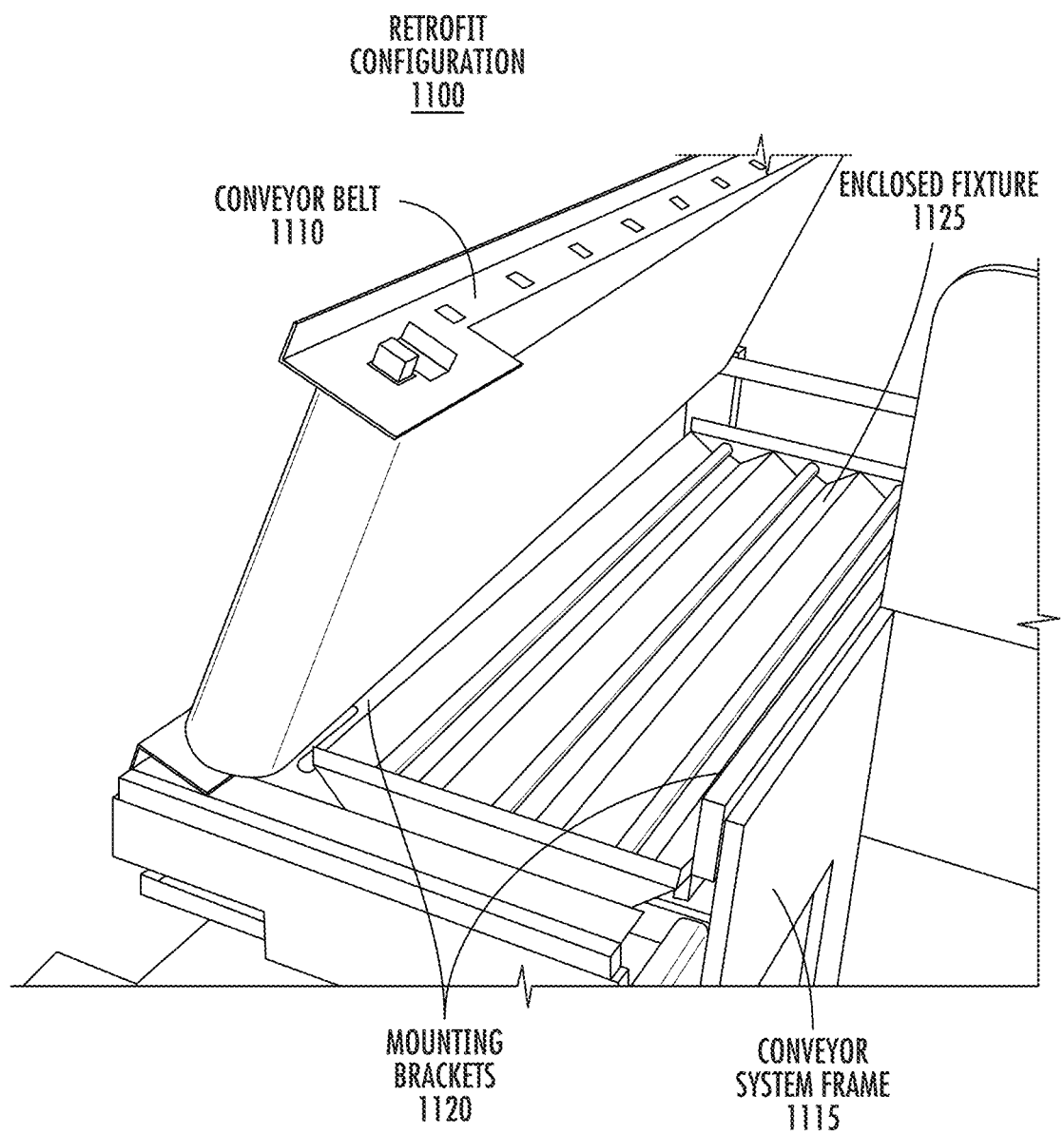
Figure 11C:
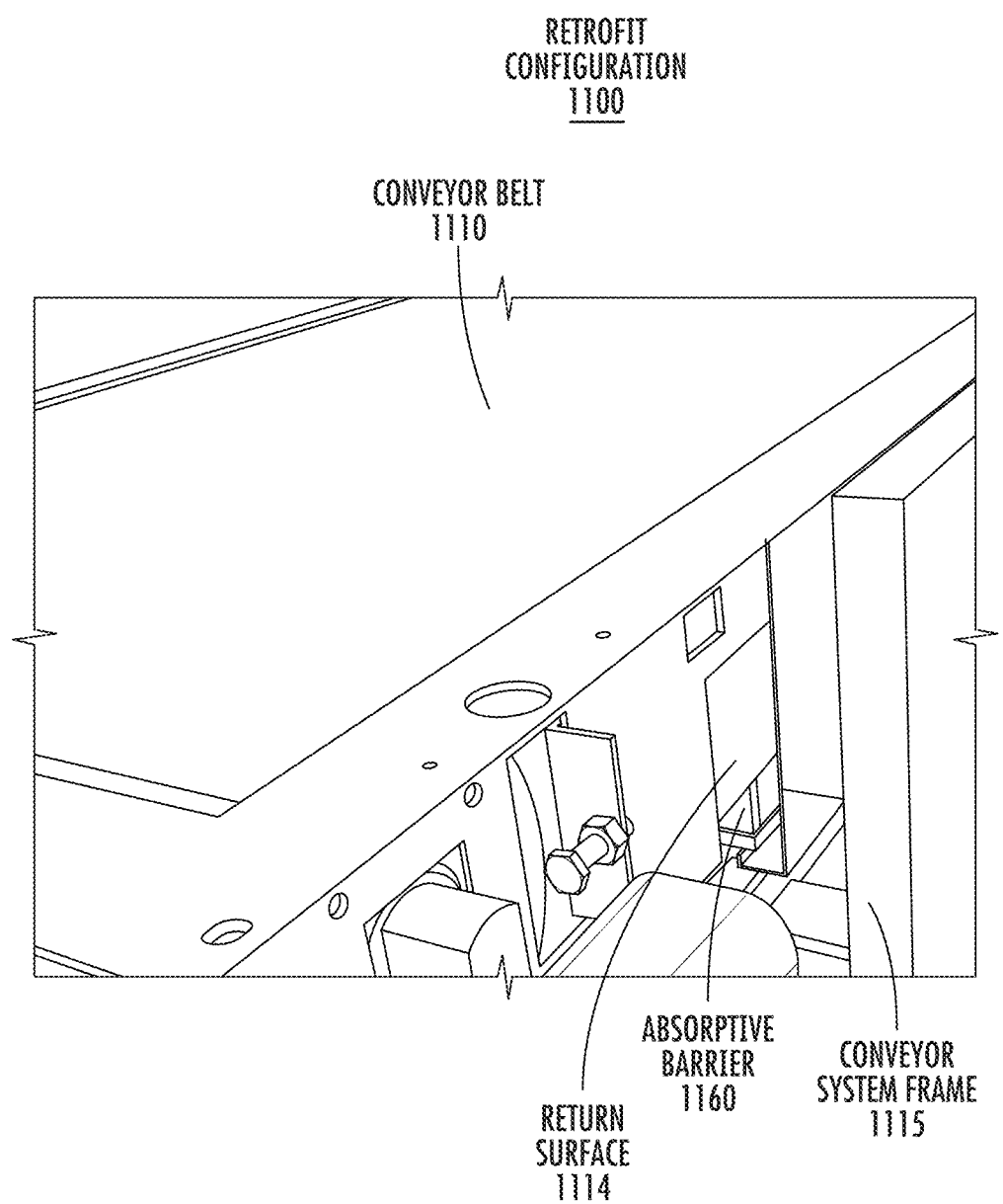

In some retrofit configurations, a UV emission device may be installed in a conveyor system via one or more access techniques. The access techniques may provide access, e.g., for an installation technician, of an area between a conveyor belt and a frame of the conveyor system. FIG. 11a depicts a view of an example retrofit configuration 1100, in which a conveyor belt 1110 is repositioned with respect to a frame 1115 of a conveyor system. FIG. 11b depicts an additional view of the retrofit configuration 1100, in which an enclosed fixture 1125 of a UV emission device is positioned on the frame 1115. FIG. 11c depicts an additional view of the retrofit configuration 1100, in which an absorptive barrier 1160 of the enclosed fixture 1125 forms an emission seal between the enclosed fixture 1125 and a return surface 1114 of the belt 1110. FIGS. 11a, 11b, and 11c are collectively referred to herein as FIG. 11. The conveyor system frame 1115 and the conveyor belt 1110 may be included in a conveyor system that has an existing configuration, such as a checkout lane in a store. In some cases, the enclosed fixture 1125 may be included in a UV emission device that is installed on the example conveyor system via the retrofit configuration 1100.

In some implementations, the retrofit configuration 1100 may include one or more mounting brackets, such as mounting brackets 1120. The enclosed fixture 1125 may be positioned on the mounting brackets 1120. In some cases, the mounting brackets 1120 may include one or more features to adjust the position of the enclosed fixture 1125, such as one or more incline rails (e.g., as described in regards to FIG. 10).

In the retrofit configuration 1100, the conveyor belt 1110 may be repositioned with respect to the frame 1115, such as by rotating (or otherwise adjusting) the conveyor belt 1110 to a vertical position with respect to the frame 1115. The repositioning of the conveyor belt 1110 may provide access to an area between the belt 1110 and the frame 1115. One or more of the mounting brackets 1120 may be positioned on features of the frame 1115, such as one or more frame rails (e.g., as described in regards to FIG. 10). In addition, the enclosed fixture 1125 may be positioned within the area between the belt 1110 and the frame 1115, such as by positioning the enclosed fixture 1125 on the mounting rails 1120. The conveyor belt 1110 may have additional repositioning, such as by rotating the belt 1110 to a horizontal position with respect to the frame 1115 (e.g., a horizontal position suitable to carry items on the belt 1110). In some cases, the position of the enclosed fixture 1125 may be adjusted on the mounting brackets 1120, such as an adjustment along incline rails of the brackets 1120. In some cases, adjustment of the position of the enclosed fixture 1125 on the brackets 1120 may provide or improve a fitted configuration between the enclosed fixture 1125 and the return surface 1114. For example, adjustment of the position of the enclosed fixture 1125 may modify an amount of pressure between the absorptive barrier 1160 and the return surface 1114.

In some cases, the retrofit configuration 1100 includes one or more additional components of the example UV emission device. For example, the UV emission device may include one or more current sense components, such as the current sensor 747 described in regards to FIG. 7. The current sense components may be applied to one or more motors of the conveyor belt 1110. In addition, the UV emission device may include a controller module, as described elsewhere herein. Furthermore, the UV emission device may include one or more interlock switches, as described elsewhere herein. The retrofit configuration 1100 may include one or more of the current sense components, interlock switches, or controller module applied to the example conveyor system receiving the retrofit configuration 1100. For example, the conveyor belt 1110 may be repositioned to a horizontal (or substantially horizontal) position in which the enclosed fixture 1125 has a fitted configuration against the conveyor about 1110. In the fitted configuration, the interlock switches may determine if an emission seal is formed between the fixture 1125 and the conveyor belt 1110. In addition, the controller module may modify output of one or more emission elements included in the fixture 1125 based on signals received from the interlock switches, the current sense components, a temperature sensor, or other received inputs, as described elsewhere herein.

Figure 12:
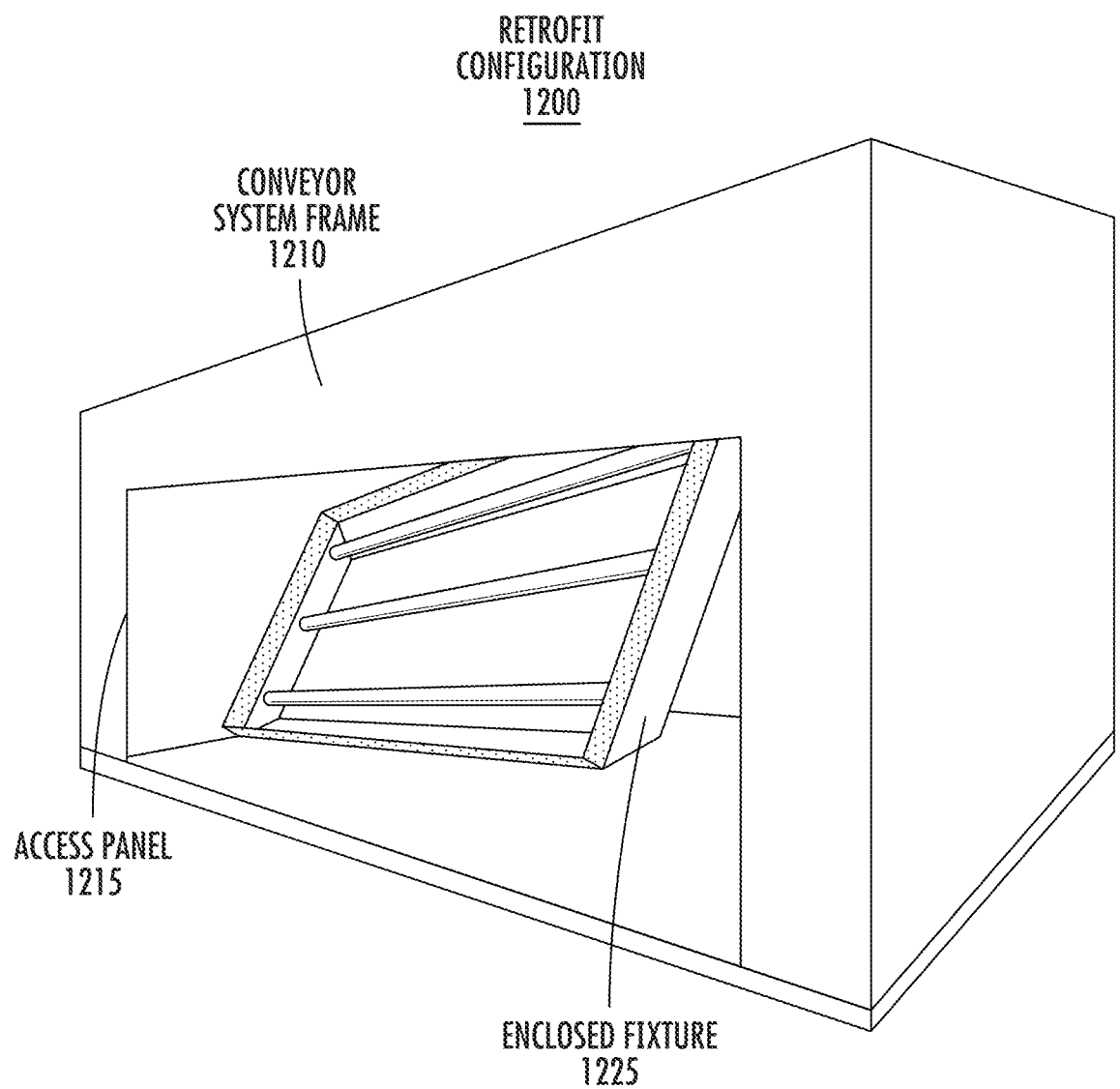
FIG. 12 is a view of an example retrofit configuration in which a frame of a conveyor system includes an access panel, according to certain implementations.

In FIG. 11, the retrofit configuration 1100 may be applied to the example conveyor system via an access technique in which the conveyor belt 1110 is rotated or otherwise has an adjusted position, but other implementations are possible. FIG. 12 depicts an example of a retrofit configuration 1200 in which an enclosed fixture 1225 is installed on a frame 1210 of an example conveyor system via an access panel 1215. For example, the access panel 1215 may be removed from (or otherwise adjusted on) the conveyor system frame 1210. One or more of the enclosed fixture 1225 or mounting rails (such as described elsewhere herein) may be installed on the example conveyor system via the access panel 1215. In some cases, a position of the enclosed fixture 1225 may be adjusted with respect to the frame 1210, such as adjustments to position the fixture 1225 within a space of the frame 1210.

Figure 13A:
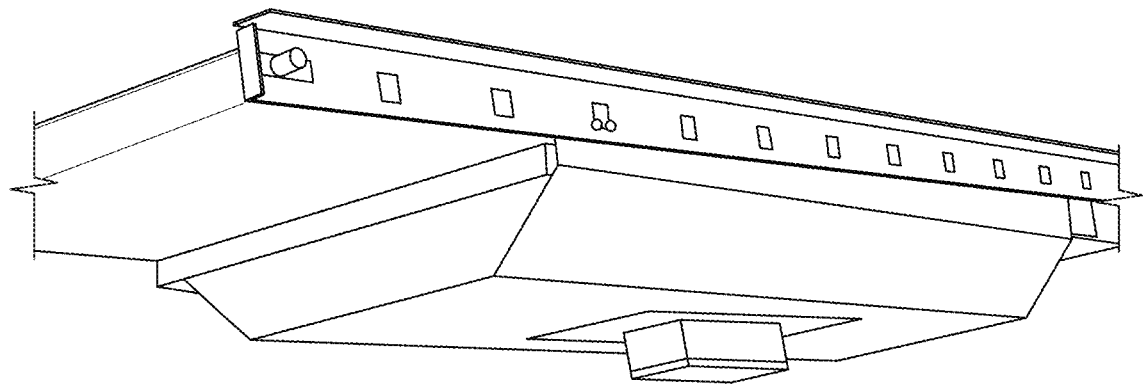
FIGS. 13a-13c are views of an example retrofit configuration in which an enclosed fixture of a UV emission device is attached to a structural element of a conveyor belt, according to certain implementations.
Figure 13B:
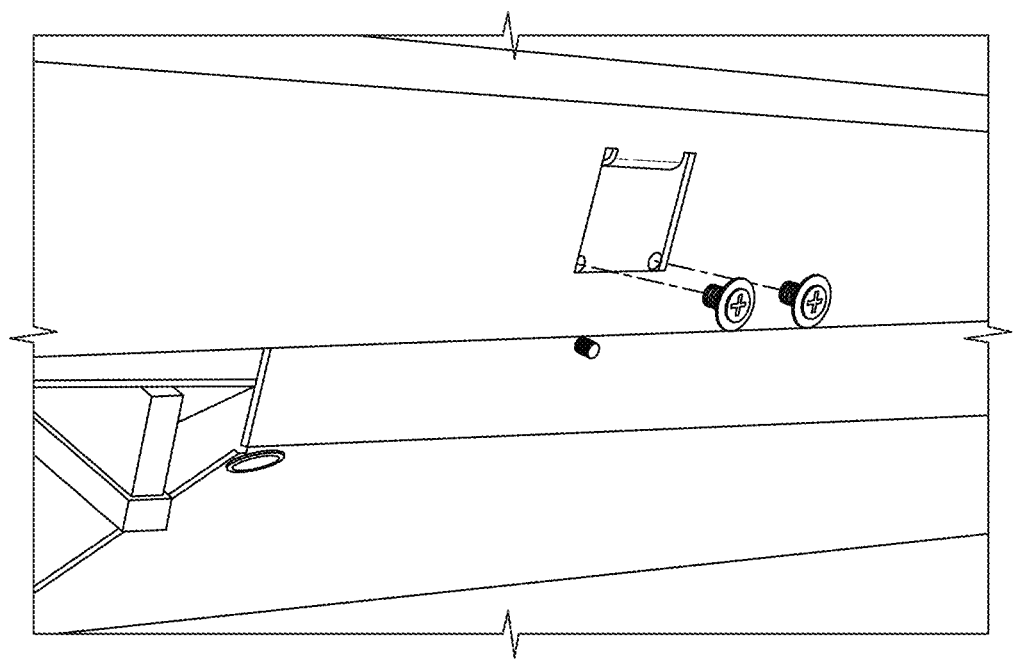
Figure 13C:
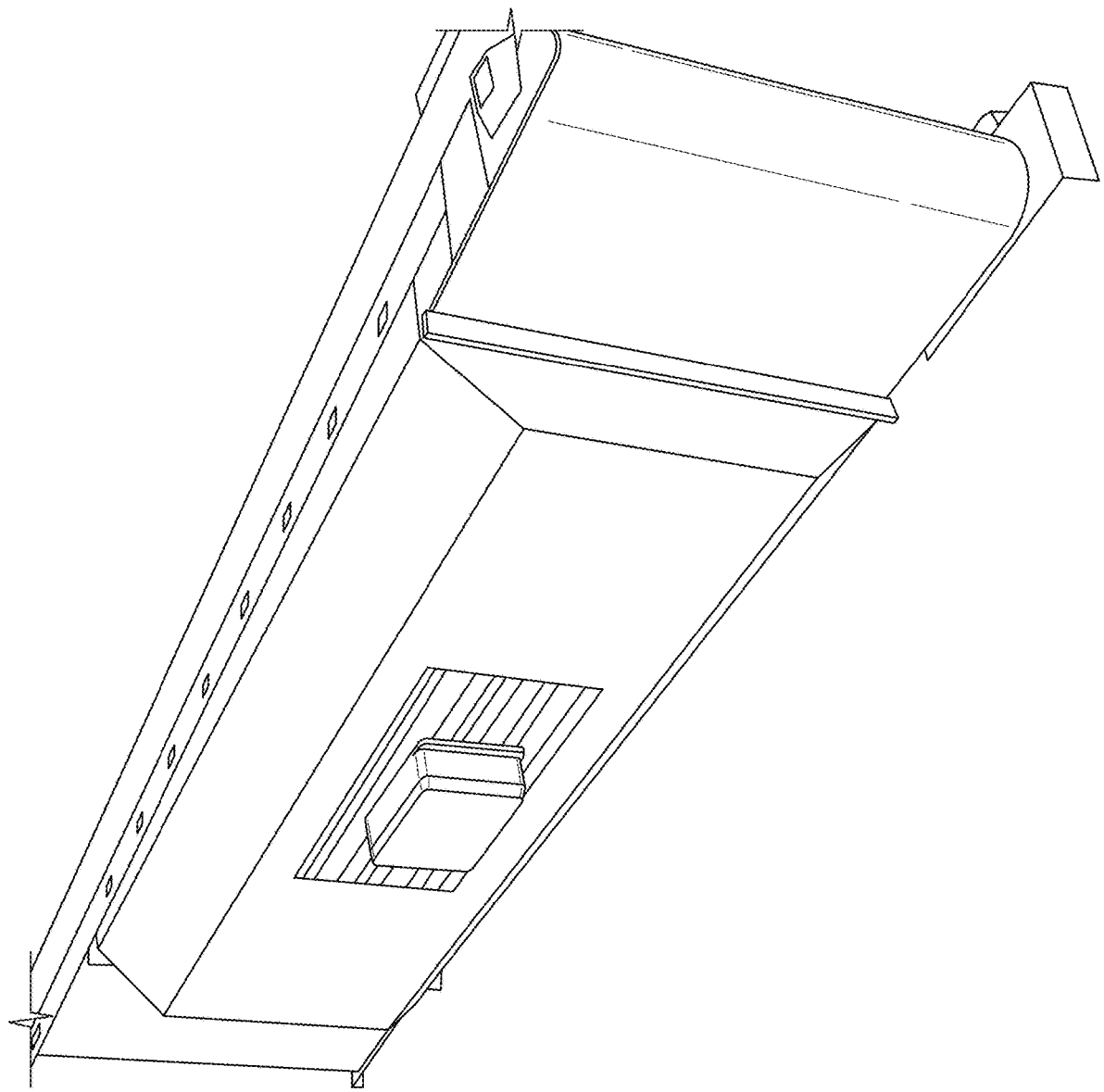

In some retrofit configurations, an enclosed fixture of a UV emission device may be attached to a structural component of a conveyor belt. FIG. 13a depicts a view of an example retrofit configuration of an enclosed fixture of a UV emission device that is attached to a support rail of a conveyor belt in a conveyor system. FIG. 13b depicts a view of an example attachment component to install the enclosed fixture to the support rail. FIG. 13c depicts an additional view of the example retrofit configuration, in which the enclosed fixture is in a fitted configuration with the conveyor belt. FIGS. 13a, 13b, and 13c are collectively referred to herein as FIG. 13.

In FIG. 13a, a housing of the enclosed fixture may be affixed to a support rail of the conveyor belt. The conveyor belt may be included in a conveyor system that has an existing configuration, such as a checkout lane in the store. In addition, the support rail may be an existing feature of the conveyor belt (e.g., present in the existing configuration of the conveyor system). In some cases, the housing may be installed via one or more features of the support rail, such as cutouts present along a length of the support rail. For example, one or more mechanical attachment components (e.g., screws, latches, nails) may affix the housing to the support rail of the conveyor belt, such as depicted in FIG. 13b.

Figure 14A:
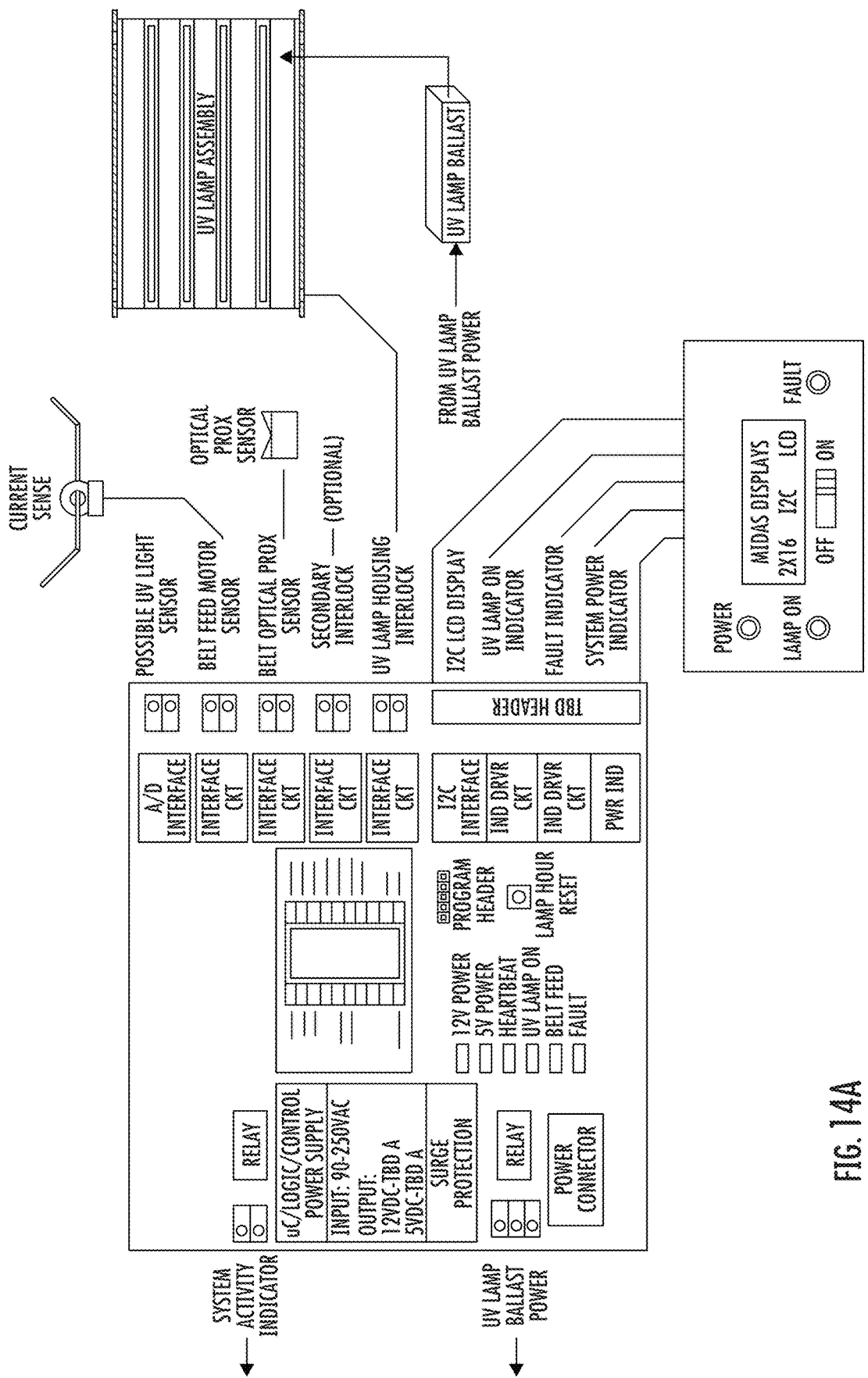
FIGS. 14a-14d are diagrams depicting example configurations of electronic components in combination with a microcontroller of a UV emission device, according to certain implementations.
Figure 14B:
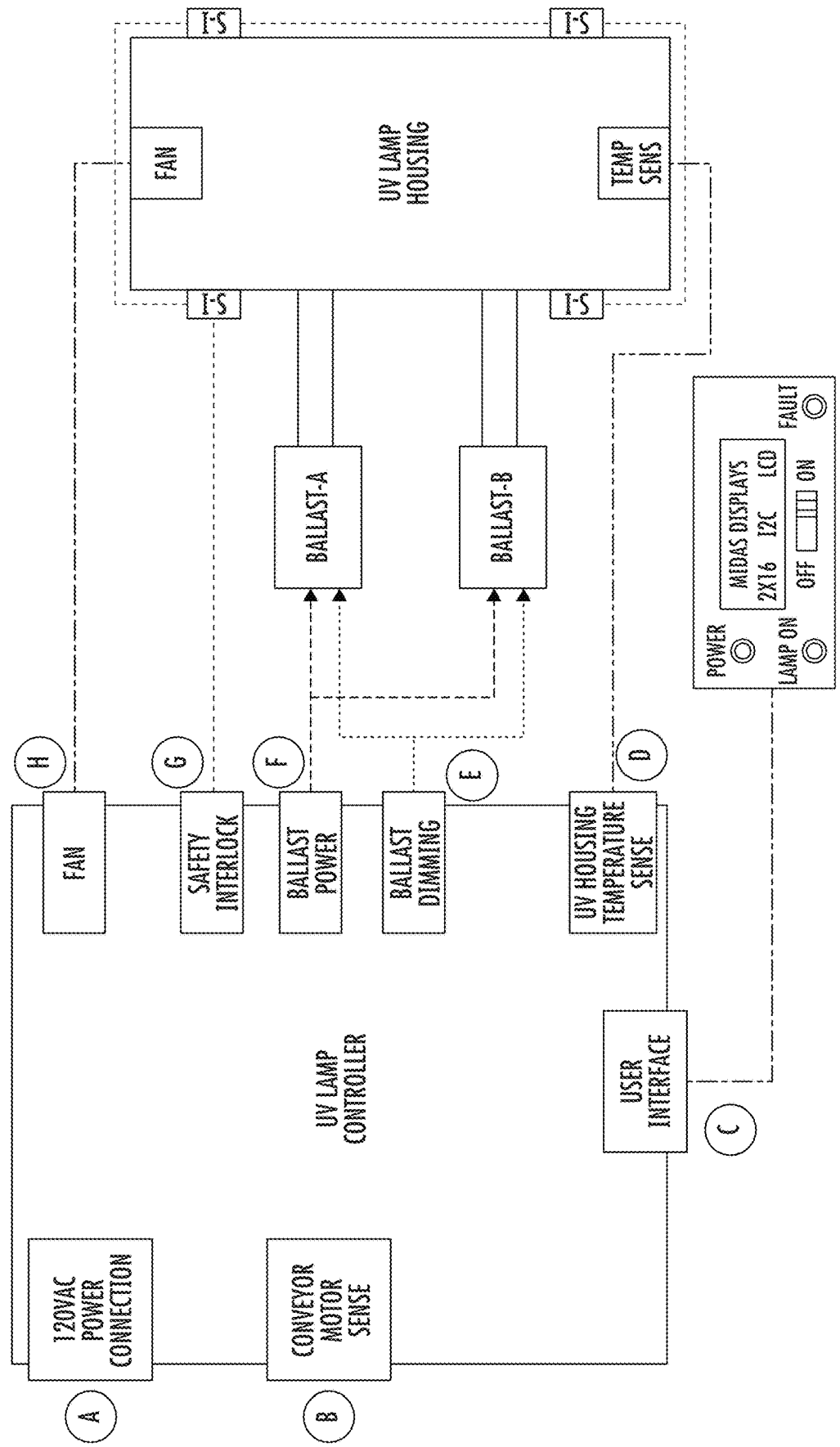
Figure 14C:
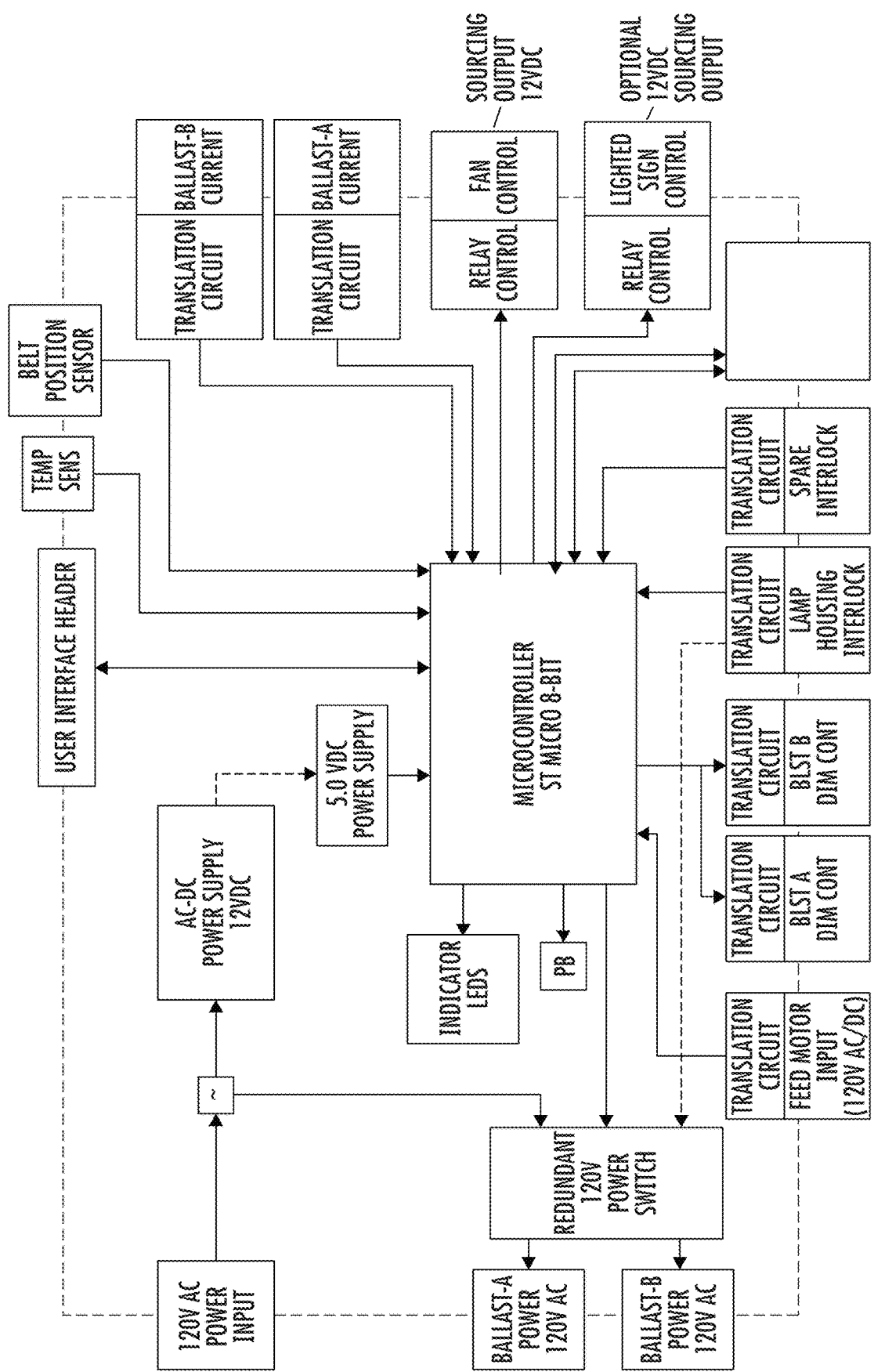
Figure 14D:
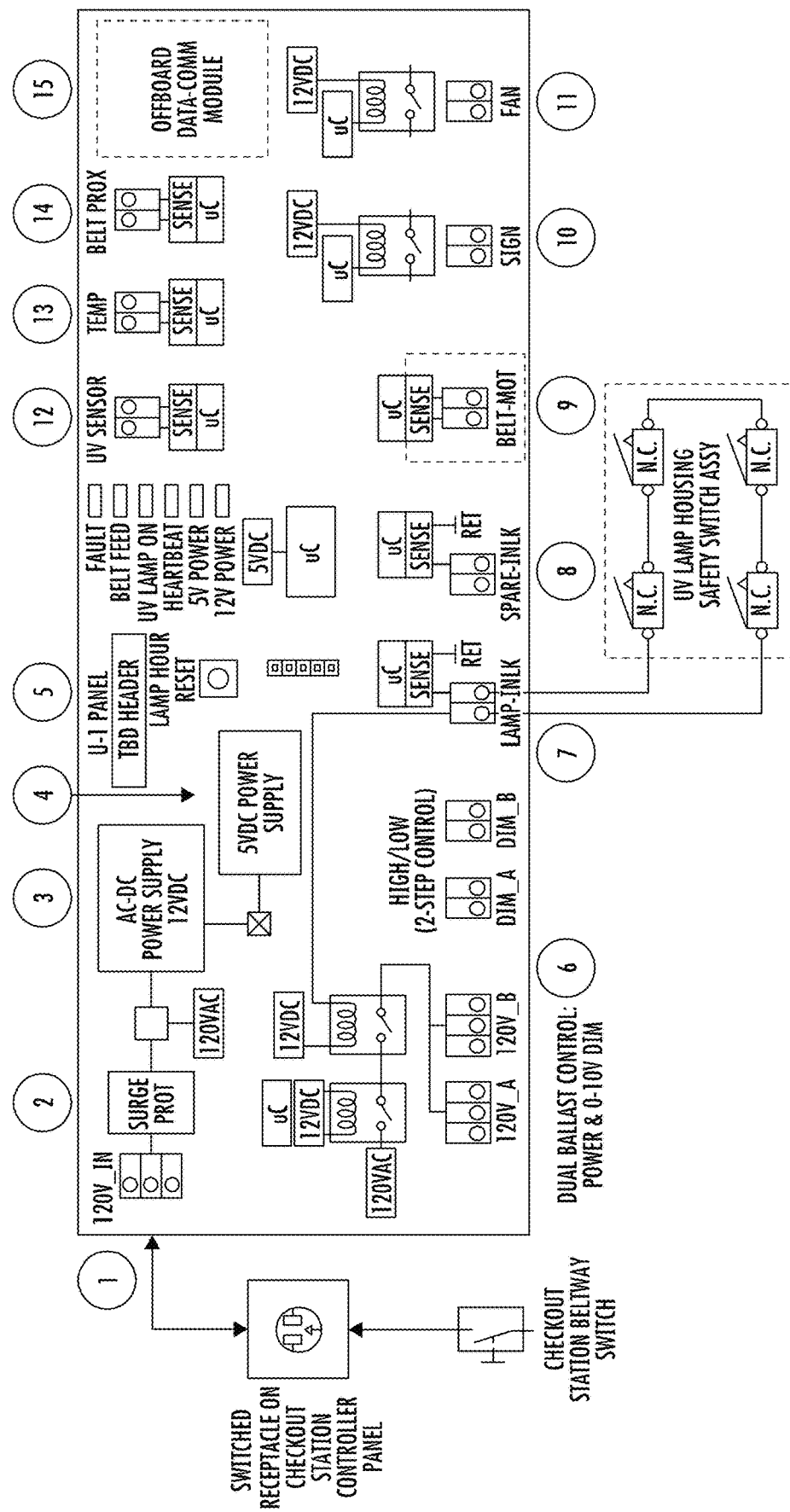
Figure 15A:
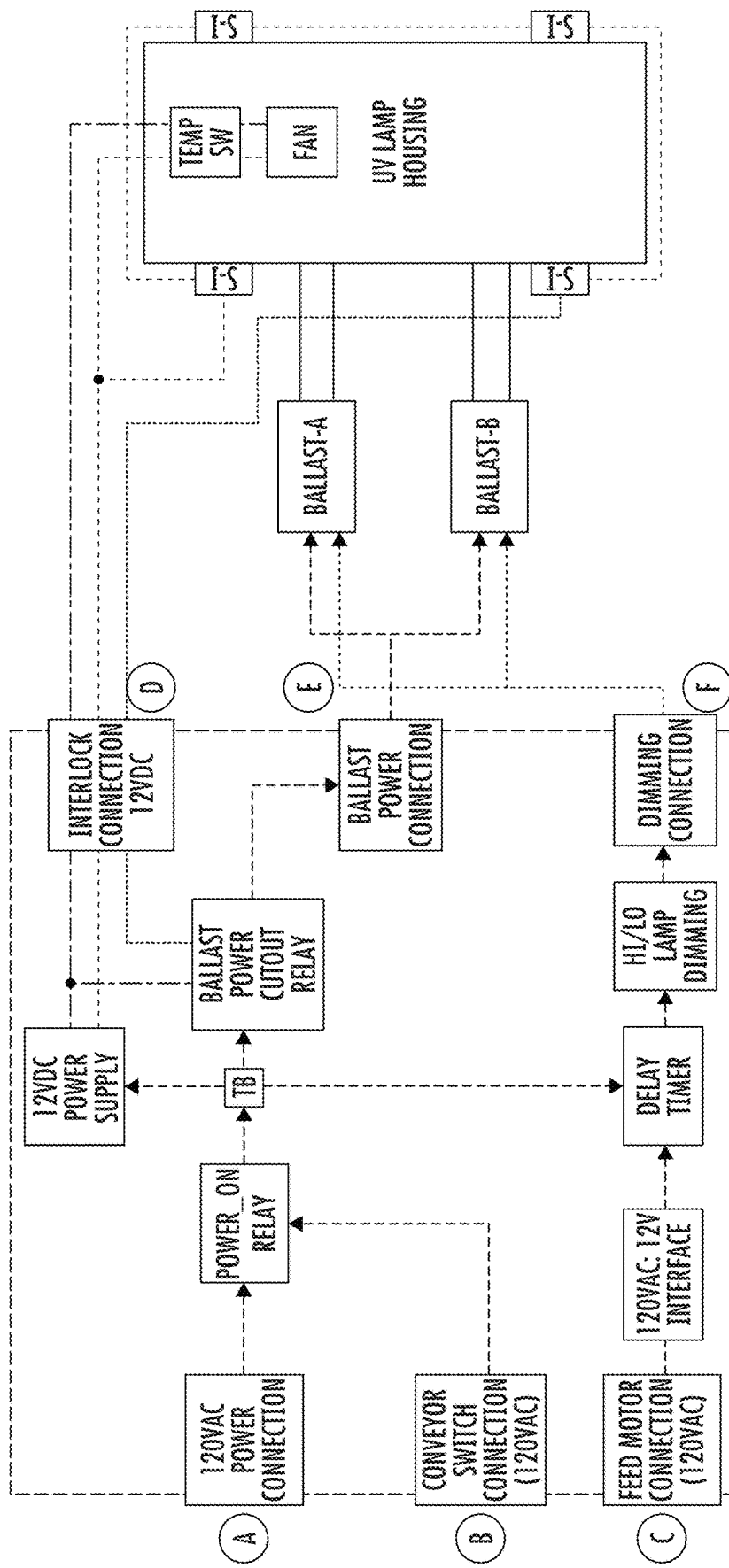
FIGS. 15a and 15b are diagrams depicting example configurations of electronic components of a UV emission device, according to certain implementations.
Figure 15B:
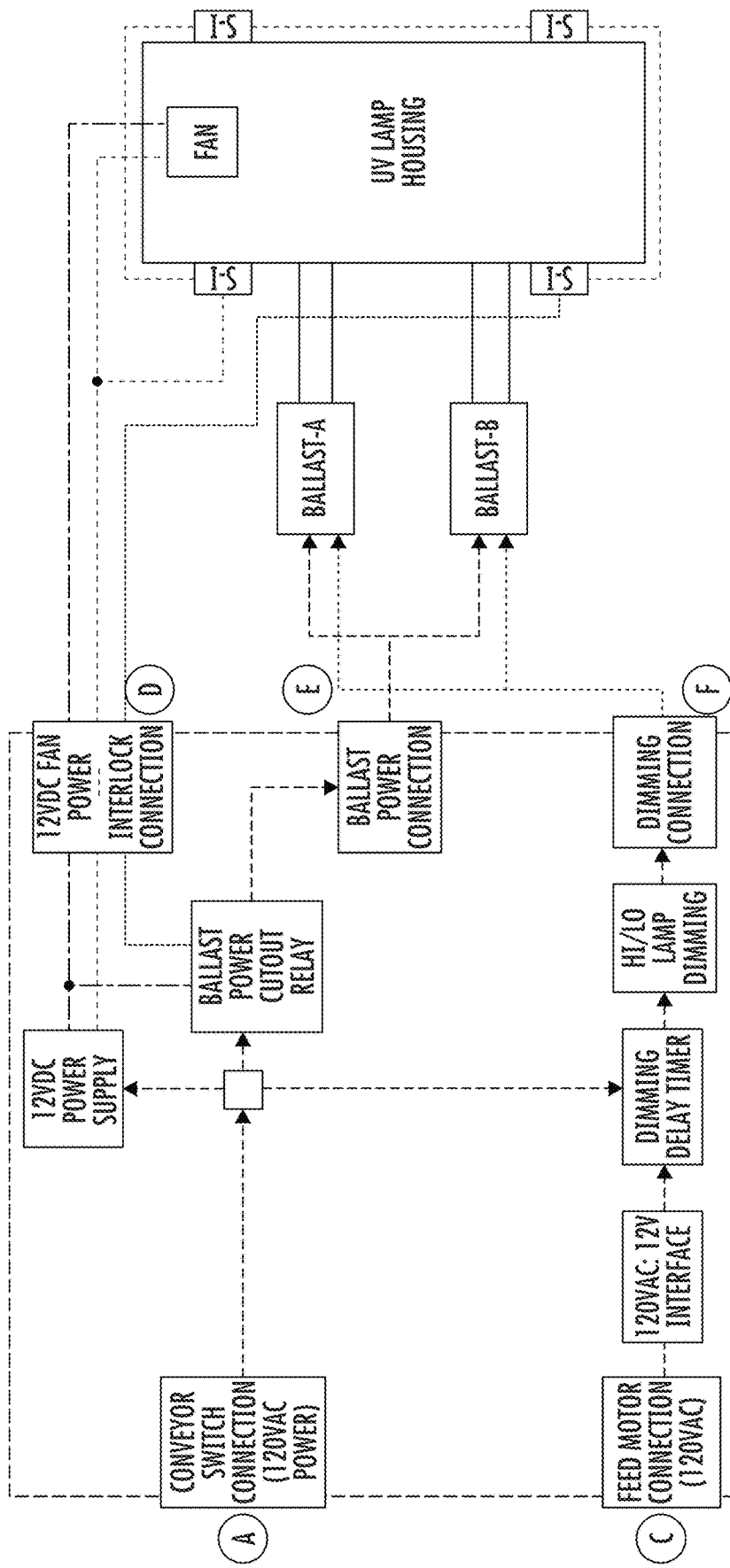

In some implementations, a controller module of a UV emission device may include one or more microcontrollers configured to perform one or more techniques described herein. The microcontrollers may be combined with additional electronic components to perform one or more described techniques. For example, one or more of the controller modules 140, 540, or 740 may include a microcontroller, connection points configured to receive or provide data signals (e.g., inputs, outputs), or other suitable electronic components. FIG. 14a is a diagram depicting an example system configuration for aspects of a UV emission device, including a printed circuit board ("PCB") on which a microcontroller and one or more connection points may be mounted. FIG. 14a depicts example connections between the PCB and additional components of the UV emission device or a conveyor system in which the UV emission device is installed, such as connections to a current sense device, the UV lamp assembly, a user interface display device, or additional suitable components. FIG. 14b is a diagram depicting an example configuration of a controller one or more emission elements of a UV emission device. In FIG. 14b, a signal from one or more interlock switches (e.g., switches "S-I") may be received by the controller, such as at an safety interlock input point G. FIG. 14c is a diagram depicting an example configuration for a PCB in a UV emission device, such as a PCB included in a controller module. FIG. 14d is a diagram depicting an additional example configuration for a PCB in a UV emission device, such as a PCB included in the controller module. FIGS. 14a, 14b, 14c, and 14d are collectively referred to herein as FIG. 14. In some implementations, a UV emission device may include one or more components that include features or aspects described in regards to FIG. 14, including combinations of features or aspects depicted in one, some, or all examples of FIG. 14. In some cases, the PCB depicted in FIG. 14d may include a UV controller with the following potential features and functions:

UV Controller—Potential Features & Functions
1. "Checkout Station Beltway Switch" can enable power to Controller
2. Surge Protection for Ballast and Controller Protection
3. 120 VAC-12 VDC SMPS can provide 12 VDC for onboard controls
4. 5 VDC Power Supply can provide power for Logic Level Controls
5. User-Interface—Offboard UI Control Panel\User-Interface
6. Controller can control power and 0-10V to (2) Ballasts
7. Lamp Housing Interlock—Controlled & monitored by the uC and series switch assembly.
8. Spare/Secondary Safety Interlock
9. Belt-Feed Motor Sense—Senses 120V power to motor, from controller.
10. Lighted Advertisement/Notification Sign Control (relay contacts)
11. UV Lamp Housing Cooling Fan
12. UV Sensor Input and/or UV Lamp Current Sensor Input
13. Lamp Housing Temperature Sensor
14. Feed Belt Proximity Sensor
15. Offboard Wired/Wireless Data Communications Module In some implementations, a UV emission device may include one or more electronic components configured to perform one or more techniques described herein. In some cases, the electronic components omit a microcontroller. FIG. 15a is a diagram depicting an example configuration of electronic components for aspects of a UV emission device. FIG. 15b is a diagram depicting an additional example configuration of electronic components for aspects of a UV emission device. FIGS. 15a and 15b are collectively referred to herein as FIG. 15. The example configurations depicted in FIG. 15 may exclude a microcontroller. In addition, the example configurations depicted in FIG. 15 may provide one or more techniques described herein, including (without limitation) modifying power to one or more emission elements (or power regulators) based on a status of an interlock switch, a temperature signal from a temperature sensor, or a motor activity signal from a conveyor belt motor; operation of one or more fans based on temperature signal from temperature sensor; or any other technique described herein. In some implementations, a UV emission device may include one or more components that include features or aspects described in regards to FIG. 15, including combinations of features or aspects depicted in one or all examples of FIG. 15.

General Considerations

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific implementations thereof, it will be appreciated that those skilled in the art, upon attaining an understanding of the foregoing, may readily produce alterations to, variations of, and equivalents to such implementations. Accordingly, it should be understood that the present disclosure has been presented for purposes of example rather than limitation, and does not preclude inclusion of such modifications, variations, and/or additions to the present subject matter as would be readily apparent to one of ordinary skill in the art.

What is claimed is:

1. A control system for an ultraviolet ("UV") emission element, the control system comprising:
a controller;
a power regulator configured to provide power to the UV energy emission element; and
an interlock switch configured to indicate a contact status between i) a moveable surface of a conveyor system and ii) an absorptive barrier configured to maintain contact with the moveable surface during motion of the moveable surface, wherein the absorptive barrier is supported via a barrier bracket arranged along an edge of a housing of the UV energy emission element, wherein the controller is configured for:
identifying, responsive to receiving a status data signal from the interlock switch, a status of the interlock switch, wherein:
a first value of the status data signal indicates a closed status of the interlock switch with respect to a first position of the barrier bracket, and
a second value of the status data signal indicates an open status of the interlock switch with respect to a second position of the barrier bracket; and
based on the identified status of the interlock switch, providing a control signal to modify power output by the power regulator, wherein:
responsive to identifying the closed status of the interlock switch, the controller provides a first control signal to the power regulator, the first control signal configuring the power regulator to provide power to the UV energy emission element, and
responsive to identifying the open status of the interlock switch, the controller provides a second control signal to the power regulator, the second control signal configuring the power regulator to decrease power to the UV energy emission element.

2. The control system of claim 1, wherein the second control signal further configures the power regulator to cause the UV energy emission element to enter a dimmed state.

3. The control system of claim 1, further comprising a current sensor configured to detect current to a motor of the conveyor system, the motor configured to drive the moveable surface,
wherein the controller is further configured for:
receiving a current sense signal from the current sensor, wherein a first value of the current sense signal indicates motor activity driving the moveable surface; and
responsive to receiving the current sense signal indicating the motor activity, providing a third control signal to the power regulator, the third control signal configuring the power regulator to provide power to the UV energy emission element.

4. The control system of claim 1, further comprising a thermal sensor configured to detect a temperature within the housing of the UV energy emission element,
wherein the controller is further configured for:
receiving a temperature signal from the thermal sensor;
determining, via a comparison of the temperature signal to a temperature threshold, that the temperature within the housing of the UV energy emission element exceeds the temperature threshold; and
responsive to determining that the temperature within the housing exceeds the temperature threshold, providing a third control signal to a fan configured to modify an airflow into or out of the housing, wherein the third control signal configures the fan to increase the airflow.

5. The control system of claim 4, wherein the controller is further configured for:
subsequent to providing the third control signal, receiving an additional temperature signal from the thermal sensor, the additional temperature signal indicating a subsequent temperature within the housing;
determining, via a comparison of the additional temperature signal to the temperature threshold, that the subsequent temperature within the housing exceeds the temperature threshold; and
responsive to determining that the subsequent temperature within the housing exceeds the temperature threshold, providing a fourth control signal to the power regulator, the fourth control signal configuring the power regulator to decrease power to the UV energy emission element.

6. The control system of claim 4, wherein the controller is further configured for determining the temperature threshold based on a data signal indicating an ambient temperature of an environment of the conveyor system.

7. The control system of claim 1, further comprising a current sensor configured to detect current to the UV energy emission element,
wherein the controller is further configured for:
receiving a current sense signal from the current sensor, wherein a value of the current sense signal indicates current received by the UV energy emission element;
determining, via a comparison of the value of the current sense signal to a current sense threshold, that the UV energy emission element is receiving insufficient current; and
responsive to determining that the UV energy emission element is receiving insufficient current, providing a third control signal to the power regulator, the third control signal configuring the power regulator to decrease power to the UV energy emission element.

8. The control system of claim 7, wherein the controller is further configured for:
responsive to determining that the UV energy emission element is receiving insufficient current, providing a data display signal, the data display signal indicating an emission element fault.

9. The control system of claim 1, the housing having a longitudinal edge and a lateral edge, wherein:
the moveable surface is configured to contact the longitudinal edge and the lateral edge, and
the interlock switch is located at an intersection of the longitudinal edge and the lateral edge, such that (i) the closed status of the interlock switch is responsive to the contact of the housing and the moveable surface at the longitudinal edge and the lateral edge and (ii) the open status of the interlock switch is responsive to an interruption of the contact of the housing and the moveable surface at the longitudinal edge and the lateral edge.

10. The control system of claim 9, wherein:
an interior of the housing is formed by the housing, the moveable surface, the longitudinal edge, and the lateral edge, and
the contact of the housing and the moveable surface at the longitudinal edge and the lateral edge encloses the UV energy emission element within the interior of the housing.

11. The control system of claim 9, wherein the absorptive barrier supported via the barrier bracket is arranged along the lateral edge of the housing such that the contact of the housing and the moveable surface at the longitudinal edge and the lateral edge includes the contact between the absorptive barrier and the moveable surface,
wherein the open status of the interlock switch is further responsive to an interruption of the contact between the absorptive barrier and the moveable surface.

12. The control system of claim 1, further comprising a motion-sensing component configured to detect a motion of one or more of the moveable surface or a motor of the conveyor system, the motor configured to drive the moveable surface, wherein the controller is further configured for:
receiving an activity signal from the motion-sensing component, wherein a first value of the activity signal indicates one or more of motion of the moveable surface or motor activity driving the moveable surface; and
responsive to receiving the activity signal, providing a third control signal to the power regulator, the third control signal configuring the power regulator to provide power to the UV energy emission element.

13. The control system of claim 1, further comprising a UV level sensor configured to detect output of the UV energy emission element, wherein the controller is further configured for:
receiving a UV level signal from the UV level sensor, wherein a value of the UV level signal indicates UV energy received by the UV level sensor;
determining, via a comparison of the value of the UV level signal to a UV energy level threshold, that the output of the UV energy emission element is reduced below the UV energy level threshold; and
responsive to determining that the output of the UV energy emission element is reduced, providing an alert signal to a building maintenance system.

14. The control system of claim 1, wherein the controller is further configured for, responsive to receiving a system operational signal, providing an alert signal to a building maintenance system.

15. The control system of claim 1, further comprising:
a first power relay configured to modify state in response to a first input signal from the interlock switch; and
a second power relay configured to modify state in response to a second input signal from the controller,
wherein, responsive to the first power relay having an open state or the second power relay having an open state, the power regulator is configured to interrupt power to the UV energy emission element.

16. A method of controlling an ultraviolet ("UV") energy emission element, the method including operations comprising:
receiving a status data signal from an interlock switch configured to indicate a contact status between i) a moveable surface of a conveyor system and ii) an absorptive barrier configured to maintain contact with the moveable surface during motion of the moveable surface, wherein the absorptive barrier is supported via a barrier bracket arranged along an edge of a housing of the UV energy emission element;
identifying, responsive to receiving the status data signal, a status of the interlock switch, wherein:
a first value of the status data signal indicates a closed status of the interlock switch with respect to a first position of the barrier bracket, and
a second value of the status data signal indicates an open status of the interlock switch with respect to a second position of the barrier bracket; and
providing a control signal to a power regulator configured to provide power to the UV energy emission element, wherein:
responsive to identifying the closed status of the interlock switch, the control signal configures the power regulator to provide power to the UV energy emission element, and
responsive to identifying the open status of the interlock switch, the control signal configures the power regulator to decrease power to the UV energy emission element.

17. The method of claim 16, wherein the control signal configuring the power regulator to decrease power to the UV energy emission element further configures the power regulator to cause the UV energy emission element to enter a dimmed state.

18. The method of claim 16, further comprising:
receiving a current sense signal, wherein a first value of the current sense signal indicates motor activity driving the moveable surface; and
responsive to receiving the current sense signal indicating the motor activity, providing a second control signal to the power regulator, the second control signal configuring the power regulator to provide power to the UV energy emission element.

19. The method of claim 16, further comprising:
receiving a temperature signal indicating a temperature within the housing of the UV energy emission element;
determining, via a comparison of the temperature signal to a temperature threshold, that the temperature within the housing of the UV energy emission element exceeds the temperature threshold; and
responsive to determining that the temperature within the housing exceeds the temperature threshold, providing a second control signal to a fan configured to modify an airflow into or out of the housing, wherein the second control signal configures the fan to increase the airflow.

20. The method of claim 19, further comprising:
subsequent to providing the second control signal, receiving an additional temperature signal indicating a subsequent temperature within the housing;
determining, via a comparison of the additional temperature signal to the temperature threshold, that the subsequent temperature within the housing exceeds the temperature threshold; and
responsive to determining that the subsequent temperature within the housing exceeds the temperature threshold, providing a third control signal to the power regulator, the third control signal configuring the power regulator to decrease power to the UV energy emission element.

21. The method of claim 16, further comprising:
receiving a current sense signal having a value that indicates a level of current received by the UV energy emission element;
determining, via a comparison of the value of the current sense signal to a current sense threshold, that the UV energy emission element is receiving insufficient current; and
responsive to determining that the UV energy emission element is receiving insufficient current, providing a second control signal to the power regulator, the second control signal configuring the power regulator to decrease power to the UV energy emission element.

22. The method of claim 21, further comprising:
responsive to determining that the UV energy emission element is receiving insufficient current, providing a data display signal, the data display signal indicating an emission element fault.

23. The method of claim 16, the housing having a longitudinal edge and a lateral edge, wherein:
the moveable surface is configured to contact the longitudinal edge and the lateral edge, and the interlock switch is located at an intersection of the longitudinal edge and the lateral edge, such that (i) the closed status of the interlock switch is responsive to the contact of the housing and the moveable surface at the longitudinal edge and the lateral edge and (ii) the open status of the interlock switch is responsive to an interruption of the contact of the housing and the moveable surface at the longitudinal edge and the lateral edge.

24. The method of claim 23, wherein:
an interior of the housing is formed by the housing, the moveable surface, the longitudinal edge, and the lateral edge, and
the contact of the housing and the moveable surface at the longitudinal edge and the lateral edge encloses the UV energy emission element within the interior of the housing.

25. The method of claim 23, wherein the absorptive barrier supported via the barrier bracket is arranged along the lateral edge of the housing such that the contact of the housing and the moveable surface at the longitudinal edge and the lateral edge includes the contact between the absorptive barrier and the moveable surface,
wherein the open status of the interlock switch is further responsive to an interruption of the contact between the absorptive barrier and the moveable surface.

* * * * *